United States Patent
Li et al.

(10) Patent No.: US 11,307,656 B2
(45) Date of Patent: Apr. 19, 2022

(54) VIEW-THROUGH SENSORS AND APPARATUSES FOR TRACKING EYE MOVEMENT, AND METHODS AND SOFTWARE THEREFOR

(71) Applicant: Trustees of Dartmouth College, Hanover, NH (US)

(72) Inventors: Tianxing Li, Hanover, NH (US); Qiang Liu, Hanover, NH (US); Xia Zhou, Hanover, NH (US)

(73) Assignee: Trustees of Dartmouth College, Hanover, NH (US)

(*) Notice: Subject to any disclaimer, the term of this patent is extended or adjusted under 35 U.S.C. 154(b) by 0 days.

(21) Appl. No.: 16/645,363

(22) PCT Filed: Sep. 14, 2018

(86) PCT No.: PCT/US2018/051164
§ 371 (c)(1),
(2) Date: Mar. 6, 2020

(87) PCT Pub. No.: WO2019/055839
PCT Pub. Date: Mar. 21, 2019

(65) Prior Publication Data
US 2021/0116995 A1 Apr. 22, 2021

Related U.S. Application Data

(60) Provisional application No. 62/703,185, filed on Jul. 25, 2018, provisional application No. 62/559,288, filed on Sep. 15, 2017.

(51) Int. Cl.
*G06F 3/01* (2006.01)
*G02B 27/01* (2006.01)

(52) U.S. Cl.
CPC ......... *G06F 3/013* (2013.01); *G02B 27/0172* (2013.01); *G02B 27/0179* (2013.01);
(Continued)

(58) Field of Classification Search
CPC . G06F 3/013; G02B 27/0172; G02B 27/0179; G02B 2027/0178; G02B 2027/0187
See application file for complete search history.

(56) References Cited

U.S. PATENT DOCUMENTS

2013/0286178 A1* 10/2013 Lewis .................... G02B 30/34
348/78
2014/0240665 A1 8/2014 Pugh et al.
(Continued)

OTHER PUBLICATIONS

International Search Report and Written Opinion dated Mar. 8, 2019, in connection with PCT/US2018/051164, filed Sep. 14, 2018.
(Continued)

*Primary Examiner* — Sahlu Okebato
(74) *Attorney, Agent, or Firm* — Downs Rachlin Martin PLLC

(57) ABSTRACT

View-through sensors each locatable proximate to an eye of a user and for use while the user is engaged in viewing activity. Each view-through sensor has a view-through region that allows the user to view through the sensor. An active peripheral region at least partially surrounds the view-through region and includes multiple light-sensing regions for sensing light reflected from an eye. In some embodiments, the view-through sensor is configured to use environmental light for eye tracking. When the view-through sensor uses environmental light, spatial and temporal information about the intensity of the environmental light can be used to enhance eye-tracking performance. This information can be obtained, for example, from light-sensing regions on the reverse side of the view-through sensor, from an electronic display, or from a forward-facing camera.

(Continued)

In some embodiments, the view-through sensor includes light-emitting regions that emit the light that the sensor uses to track eye movement.

28 Claims, 15 Drawing Sheets

(52) U.S. Cl.
CPC .............. *G02B 2027/0178* (2013.01); *G02B 2027/0187* (2013.01)

(56) References Cited

U.S. PATENT DOCUMENTS

| | | |
|---|---|---|
| 2015/0316982 A1 | 11/2015 | Miller |
| 2015/0324692 A1* | 11/2015 | Ritchey .................. A61B 5/055 348/14.08 |
| 2016/0033772 A1* | 2/2016 | Han ..................... H04N 1/6083 359/630 |
| 2016/0349516 A1 | 12/2016 | Alexander et al. |
| 2017/0091549 A1* | 3/2017 | Gustafsson ........... G02B 27/017 |
| 2020/0150508 A1* | 5/2020 | Patterson ................ H02J 50/80 |

OTHER PUBLICATIONS

Ozawa et al. "Wearable line-of-sight detection system using micro-fabricated transparent optical sensors on eyeglasses." In: Sensors and Actuators A 205 (2014) 208-214., [online] [retrieved on Feb. 19, 2019 (Feb. 19, 2019)] Retrieved from the Internet <URL: https://www.sciencedirect.com/science/article/pii/S0924424713005827, entire document, especially Abstract: pp. 1-5.

* cited by examiner

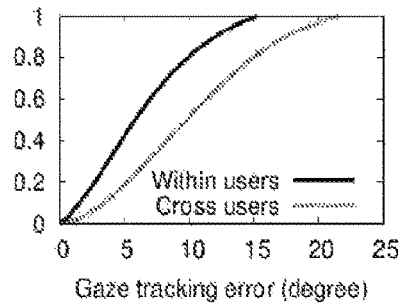
(a) CDF of gaze tracking error
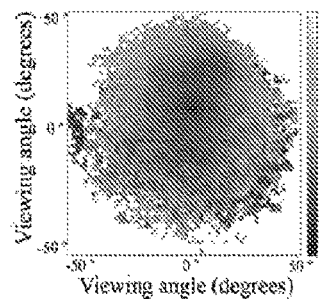
(b) Error distribution (within user)
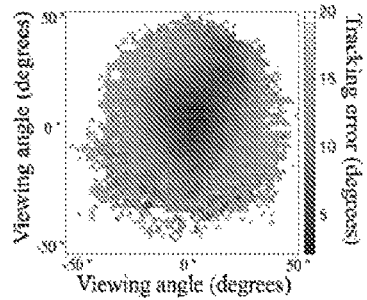
(c) Error distribution (cross user)
FIG. 13A     FIG. 13B     FIG. 13C
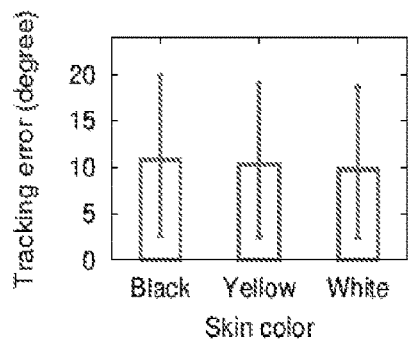
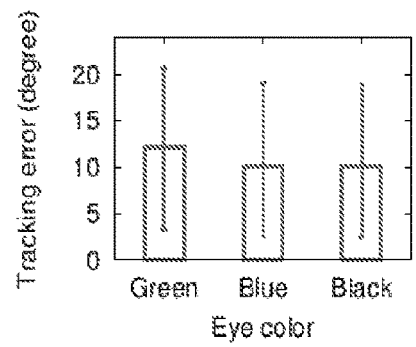
FIG. 14A     FIG. 14B
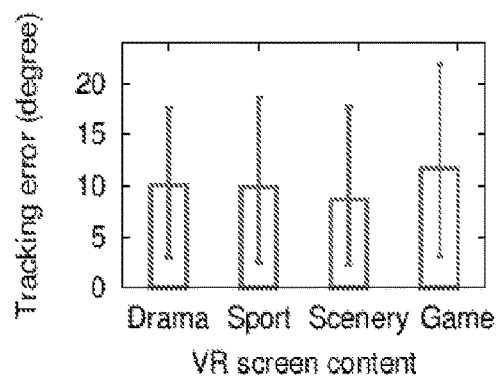
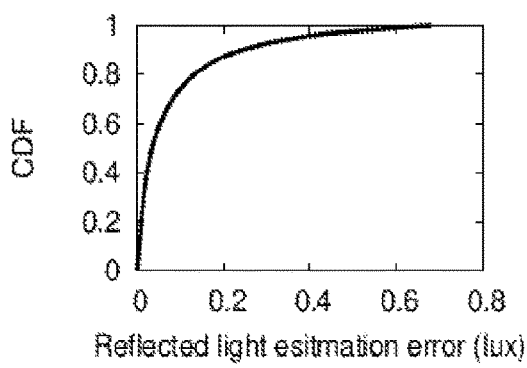
FIG. 15     FIG. 16

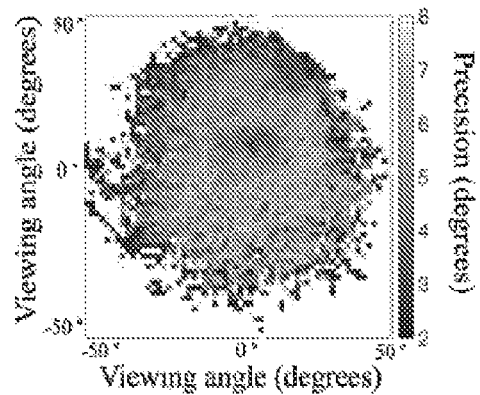 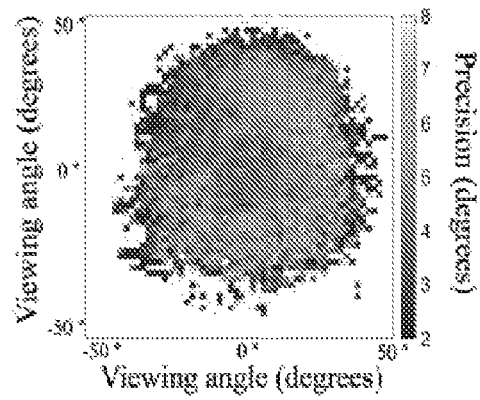
(a) Within user  (b) Cross user
FIG. 17A  FIG. 17B
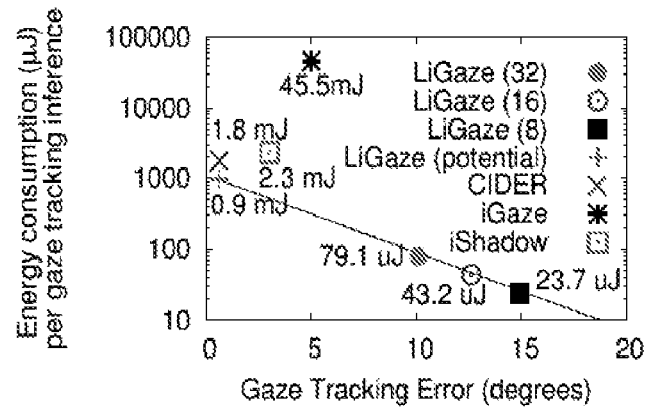
FIG. 18
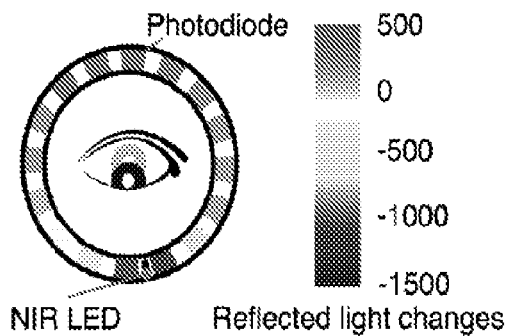 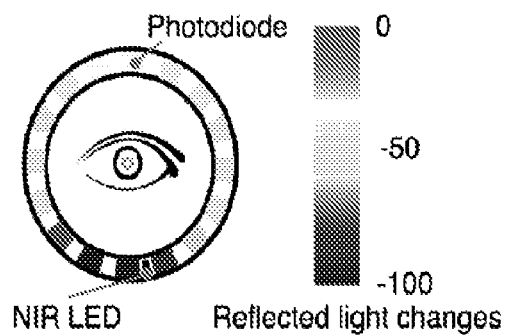
(a) Pupil movement  (b) Pupil size variation
FIG. 19A  FIG. 19B (a) Fixation (b) Smooth pursuit (c) Saccade (d) Mixed eye movement (a) Pupil position (b) Pupil diameter (c) Error distribution (d) User activity

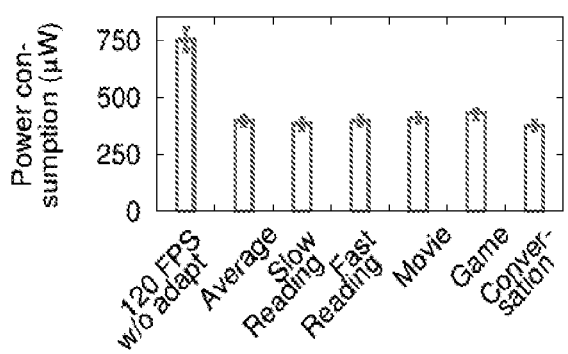
(a) Across activities
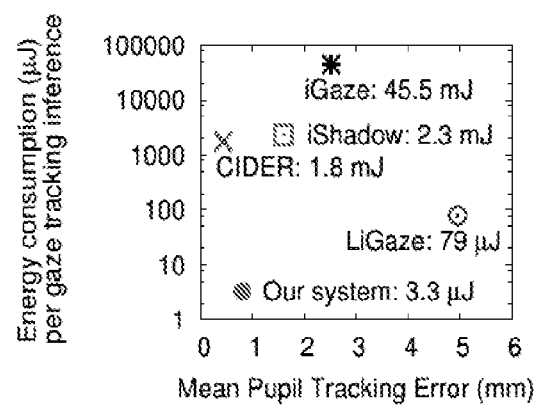
(b) Comparison to existing systems
FIG. 28A　　　　　　FIG. 28B
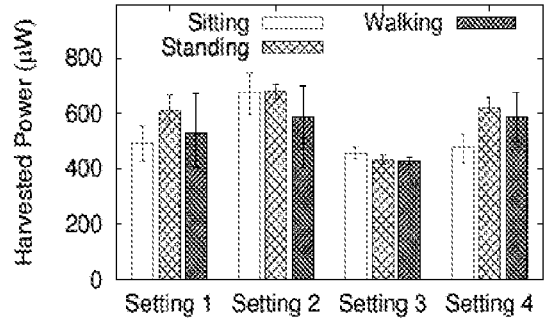
(a) Daytime
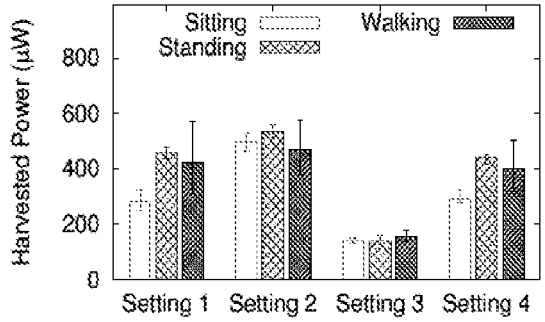
(b) Nighttime
FIG. 29A　　　　　　FIG. 29B
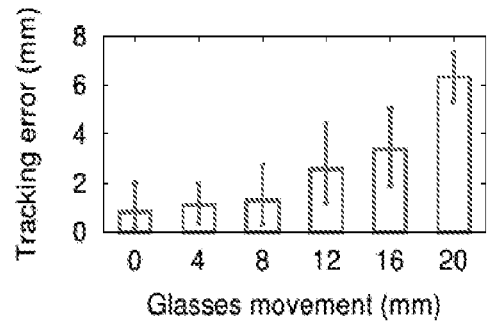
(a) Glasses movement
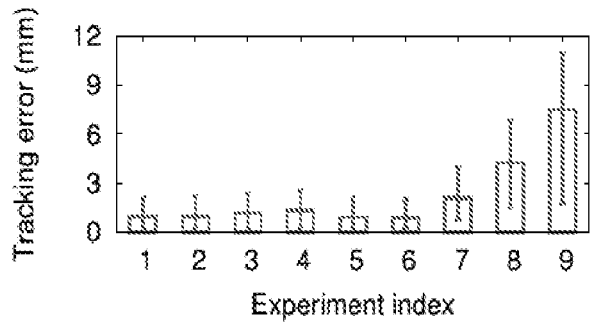
(b) Ambient light
FIG. 30A　　　　　　FIG. 30B Table 3
Front sensor (facing display)

| | | T | TR | R | BR | B | BL | L | TL |
|---|---|---|---|---|---|---|---|---|---|
| Back sensor (facing eye) | T | 0.48 | 0.75 | 0.87 | 0.87 | 0.96 | 0.81 | 0.59 | 0.54 |
| | TR | 0.69 | 0.55 | 0.76 | 0.76 | 0.79 | 0.91 | 0.88 | 0.78 |
| | R | 0.66 | 0.64 | 0.55 | 0.67 | 0.79 | 0.83 | 0.93 | 0.89 |
| | BR | 0.86 | 0.79 | 0.62 | 0.51 | 0.64 | 0.74 | 0.76 | 0.84 |
| | B | 0.97 | 0.83 | 0.68 | 0.55 | 0.50 | 0.51 | 0.78 | 0.79 |
| | BL | 0.84 | 0.90 | 0.89 | 0.86 | 0.85 | 0.61 | 0.60 | 0.58 |
| | L | 0.80 | 0.91 | 0.92 | 0.78 | 0.65 | 0.49 | 0.52 | 0.58 |
| | TL | 0.66 | 0.88 | 0.89 | 0.91 | 0.86 | 0.78 | 0.52 | 0.47 |

FIG. 31

VIEW-THROUGH SENSORS AND APPARATUSES FOR TRACKING EYE MOVEMENT, AND METHODS AND SOFTWARE THEREFOR

RELATED APPLICATION DATA

This application claims the benefit of priority of U.S. Provisional Patent Application Ser. No. 62/559,288, filed Sep. 15, 2017, and titled "ULTRA-LOW POWER GAZE TRACKING FOR VIRTUAL REALITY". This application also claims the benefit of priority of U.S. Provisional Patent Application Ser. No. 62/703,185, filed Jul. 25, 2018, and titled "LOW POWER EYE TRACKING DEVICE". Each of these applications is incorporated by reference herein in its entirety.

FEDERALLY SPONSORED RESEARCH OR DEVELOPMENT

This invention was made with government support under CNS1552924 awarded by the National Science Foundation. The government has certain rights in the invention.

FIELD OF THE INVENTION

The present invention generally relates to the field of apparatus for tracking eye movement. In particular, the present invention is directed to view-through sensors and apparatuses for tracking eye movement, and methods and software thereof.

BACKGROUND

Eye movement is a vital biological marker. Accurate and continuous monitoring of eye movement is critical for understanding its correlation with cognitive processes, identifying early symptoms of health issues (e.g., mental disorders, attention deficit, cognitive dysfunctions), and assessing the effectiveness of clinical treatments.

It is also crucial for the development of human-to-computer interaction by allowing hands-free, attentive user interfaces, and the apprehension of user affective states. Supporting such applications requires eye tracking at a submillimeter level at high tracking rates, because eye movement manifests ballistic, rapid (e.g., 500°/s) scanning movements, referred to as "saccades," mixed with eye fixations ($\approx$200 milliseconds on average). Real-time, accurate measures of these eye movement stages are essential. As examples, detection of mental disorders (e.g., depression, schizophrenia, Alzheimer's disease) requires eye tracking with less than 1° error and at least 60 Hz to extract statistics of saccadic eye movement control and eye fixation duration; in interactive applications such as tracking user's reading on a computer screen, 1° eye rotation maps to 3.25 characters on a screen 60 cm away. Additionally, to facilitate long-term deployment, the eye tracker needs to be portable and low-power, eliminating the need of frequent charging and imposing minimal burden on the wearer.

Existing technologies for wearable eye trackers still fall short in achieving these goals, at least partly because of the inherent conflict between high tracking performance and low power consumption. Conventional eye trackers use cameras to capture eye images and apply intensive image processing to identify the pupil position. As a result, high-end eye trackers typically entail a prohibitive cost (e.g., $15,000+ for a wearable eye tracker). These systems also typically require external battery packs that can be cumbersome to carry for day-to-day eye monitoring. Recent studies have analyzed the tradeoff between performance and energy for camera-based wearable eye trackers and designed techniques to drive down system energy consumption. The latest design is projected to consume tens of milliwatts to support tracking rates above 100 Hz with sub-millimeter mean tracking accuracy.

Therefore, there is a need for a wearable eye tracking device that can operate at high tracking rates (above 100 Hz) with sub-millimeter accuracy, while consuming power at microwatt levels (e.g., a low-power or ultra-low-power device).

In an example specific application, tracking a user's eye fixation direction is crucial to virtual reality (VR): it eases the user's interaction with the virtual scene and enables intelligent rendering to improve the user's visual experiences and save system energy. Existing gaze-tracking technology commonly requires cameras and active infrared emitters. Such systems raise concerns regarding energy consumption, cost, and form factor for VR headsets (especially mobile VR headsets). As a result, most existing VR headsets forgo the functionality of gaze tracking, and resort to head direction as a coarse, and often incorrect, estimate of gaze. The few proposed methods that do not require cameras either still need infrared emitters or need dense arrays of photodiodes and hardware modifications of the display.

Therefore, there is a need for a low-cost, low-power approach to gaze tracking and, in particular, gaze tracking tailored to VR.

SUMMARY OF THE DISCLOSURE

In one implementation, the present disclosure is directed to an apparatus for tracking eye movement of a subject eye of a user, wherein the subject eye has a pupil and an exterior. The apparatus includes a support structure; a view-through sensor secured to the support structure for tracking eye movement via light reflected from the exterior of the eye when the user is wearing the support structure, the view-through sensor having a view-through region that allows the user to see through the view-through sensor substantially unobstructed during use of the apparatus; and a peripheral active device region adjacent to the view-through region and at least partially surrounding the view-through region, the active peripheral device region containing first plurality of light-sensing regions located and able, separately from one another, to sense intensity of light reflecting off of the exterior of the subject eye and striking the at least four light-sensing regions.

In another implementation, the present disclosure is directed to a method of tracking movement of a subject eye of a user, wherein the subject eye has a pupil and an exterior. The method is executed by a processor and includes receiving light-intensity readings from a plurality of light-sensing regions located proximate to the subject eye, wherein the light-intensity readings are for light reflected from the exterior of the subject eye; executing a gaze-inference algorithm that determines a location of the pupil as a function of the light-intensity readings; and executing, in concert with the executing of the gaze-inference algorithm, a predictive inferencing algorithm that predicts a future location of the pupil.

In yet another implementation, the present disclosure is directed to a method of tracking movement of a subject eye of a user, wherein the subject eye has a pupil and an exterior. The method is executed by a processor and includes receiving first light-intensity readings from a plurality of first light-sensing regions located proximate to the subject eye and facing the user, wherein the light-intensity readings are for environmental light reflected from the exterior of the subject eye; receiving intensity information about the environmental light reflected from the exterior of the subject eye; extracting features from the first light-intensity readings using the first light-intensity readings and the intensity information about the environmental light; and inferring gaze of the subject eye as a function of the features extracted from the first light-intensity readings.

In still another implementation, the present disclosure is directed to a method of tracking movement of a subject eye of a user, wherein the subject eye has a pupil and an exterior. The method is executed by a processor and includes causing a plurality of emitting regions located proximate to the subject eye to sequentially emit light; when each of the plurality of emitting regions is emitting, receiving light-intensity readings from a plurality of light-sensing regions located proximate to the subject eye and facing the user, wherein the light-intensity readings are for the emitted light reflected from the exterior of the subject eye; and inferring a position of the pupil of the subject eye as a function of the light-intensity readings from the sequential emissions.

In a further implementation, the present disclosure is directed to a memory containing machine-executable instructions for performing a method of tracking movement of a subject eye of a user, wherein the subject eye has a pupil and an exterior. The method includes receiving light-intensity readings from a plurality of light-sensing regions located proximate to the subject eye, wherein the light-intensity readings are for light reflected from the exterior of the subject eye;

executing a gaze-inference algorithm that determines a location of the pupil as a function of the light-intensity readings; and executing, in concert with the executing of the gaze-inference algorithm, a predictive inferencing algorithm that predicts a future location of the pupil.

In still yet another implementation, the present disclosure is directed to a memory containing machine-executable instructions for performing a method of tracking movement of a subject eye of a user, wherein the subject eye has a pupil and an exterior. The method is executed by a processor and includes receiving first light-intensity readings from a plurality of first light-sensing regions located proximate to the subject eye and facing the user, wherein the light-intensity readings are for environmental light reflected from the exterior of the subject eye; receiving intensity information about the environmental light reflected from the exterior of the subject eye; extracting features from the first light-intensity readings using the first light-intensity readings and the intensity information about the environmental light; and inferring gaze of the subject eye as a function of the features extracted from the first light-intensity readings In another implementation, the present disclosure is directed to a memory containing machine-executable instructions for performing a method of tracking movement of a subject eye of a user, wherein the subject eye has a pupil and an exterior. The method is executed by a processor and includes causing a plurality of emitting regions located proximate to the subject eye to sequentially emit light; when each of the plurality of emitting regions is emitting, receiving light-intensity readings from a plurality of light-sensing regions located proximate to the subject eye and facing the user, wherein the light-intensity readings are for the emitted light reflected from the exterior of the subject eye; and inferring a position of the pupil of the subject eye as a function of the light-intensity readings from the sequential emissions.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 13A is a graph of cumulative distribution function (CDF) versus gaze tracking error;

FIG. 13B is a scattergram of within-user error distribution;

FIG. 13C is a scattergram of cross-user error distribution;

FIG. 14A is a diagram illustrating impact of skin color on accuracy of a prototype VTET sensor;

FIG. 14B is a diagram illustrating impact of eye color on accuracy of the prototype VTET sensor of FIG. 14A;

FIG. 15 is a diagram illustrating impact of VR content on accuracy of the prototype VTET sensor of FIG. 14A;

FIG. 16 is a diagram illustrating accuracy in estimating reflected light for the prototype VTET sensor of FIG. 14A;

FIG. 17A is a diagram illustrating within-user precision of gaze tracking for the prototype VTET of FIG. 14A;

FIG. 17B is a diagram illustrating cross-user precision of gaze tracking for the prototype VTET of FIG. 14A;

FIG. 18 is a diagram illustrating tradeoff between energy and tracking accuracy for the prototype VTET sensor of the present disclosure and several conventional low-power gaze-trading systems;

FIG. 19A is a diagram illustrating changes in light reflected from an eye when the pupil moves from center to bottom;

FIG. 19B is a diagram illustrating changes in light reflected from an eye when the pupil of a centered eye dilates;

FIG. 20A is a diagram of an example NIR VTET sensor, illustrating the layout of 6 NIR LEDs and 12 photodiodes for a left eye, viewing from a wearer's perspective;

FIG. 20B is a diagram illustrating changes in reflected light caused by pupil movement when each of the NIR LEDs of FIG. 20A is individually turned on;

FIG. 28A is a graph of power consumption of the prototype VTET apparatus of FIG. 25A across activities with and without adaption;

FIG. 28B is a graph comparing energy consumption of the prototype VTET apparatus of FIG. 25A and existing eye-tracking systems;

FIG. 29A is a graph illustrating harvested power from indoor lighting in four daytime settings while a user is wearing the prototype VTET apparatus of FIG. 25A;

FIG. 29B is a graph illustrating harvested power from indoor lighting in four nighttime settings while a user is wearing the prototype VTET apparatus of FIG. 25A;

FIG. 30A is a graph illustrating impact of eyeglass movement on tracking performance of the prototype VTET apparatus of FIG. 25A;

FIG. 30B is a graph illustrating impact of ambient light on tracking performance of the prototype VTET apparatus of FIG. 25A; and FIG. 31 contains Table 3 referenced in the Detailed Description below.

DETAILED DESCRIPTION

1. Introduction

In some aspects, the present disclosure is directed to apparatuses and systems for tracking movement of a person's eye by measuring light reflected from the eye using a view-through eye-tracking (VTET) sensor. Generally, VTET sensors and VTET apparatuses operate on the phenomenon that the pupil of an eye absorbs light directed toward the eye, while the exterior surface of the eye reflects such light. By locating a VTET sensor having multiple light-sensing regions close to the eye, movement of the pupil to differing positions causes light-sensing regions more proximate to the eye to sense lower light levels. This effect is used to continually estimate pupil location and, hence, eye movement. Further details on the operation of VTET sensors and VTET apparatuses made in accordance with the present disclosure are described below in Sections 2 and 3.

Figure 1:
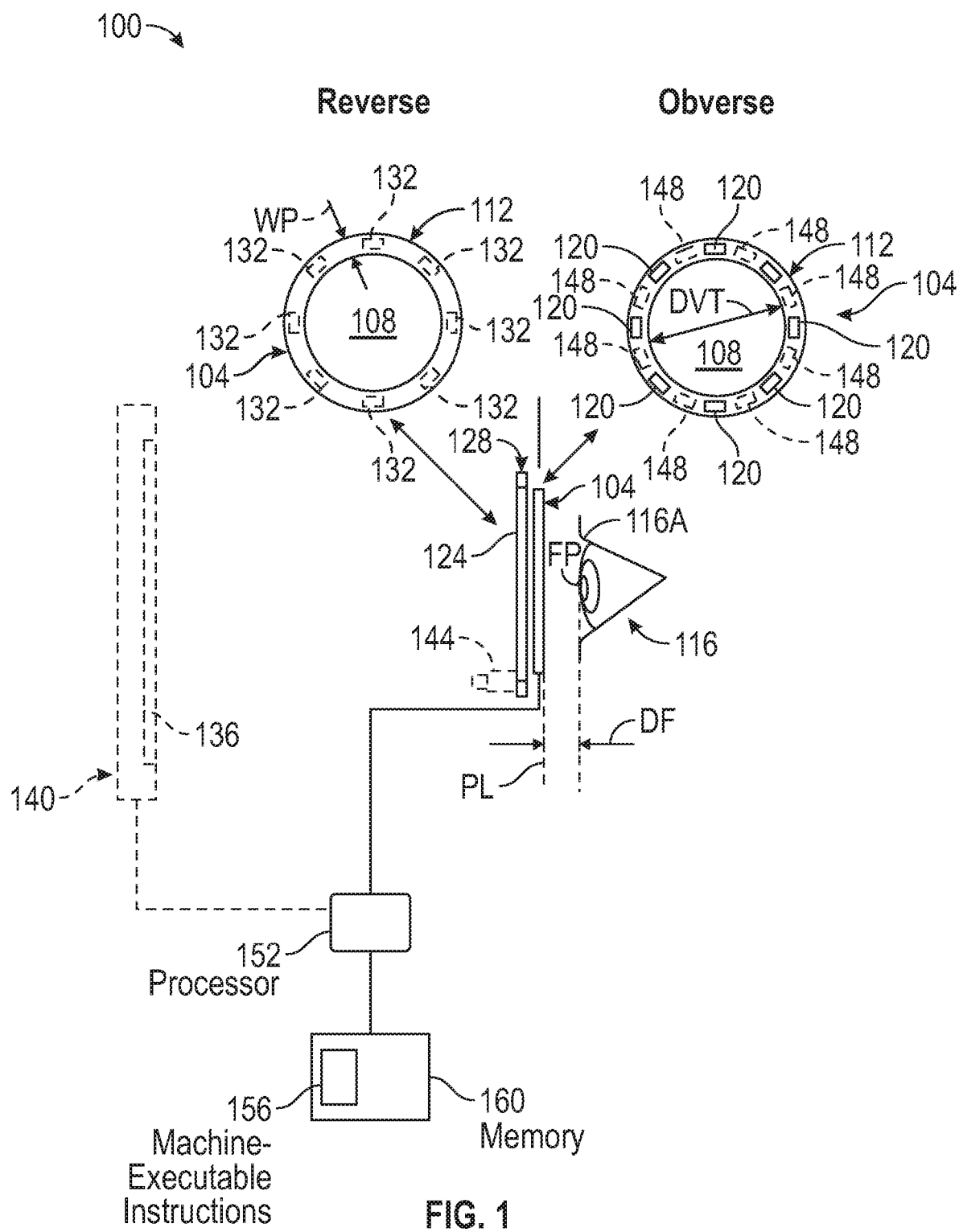
FIG. 1 is a partial schematic/partial block diagram of an example view-through eye-tracking (VTET) system made in accordance with aspects of the present disclosure.

Turning now to the drawings, FIG. 1 illustrates an example VTET apparatus 100 that includes a VTET sensor 104. As will be understood from reading this entire disclosure, VTET sensor 104 may be particularly configured such that the light reflected from the eye and used to effect eye-tracking is either environmental light, i.e., light from outside VTET apparatus 100, or light generated by the VTET apparatus. A detailed example is provided for each of the two types of reflected light. Before describing features of VTET sensor 104 and VTET apparatus 100, it is noted that the term "light" as used herein and in the appended claims is not limited to visible light but rather encompasses electromagnetic energy in frequency bands adjacent to the visible light frequency band of the electromagnetic spectrum. Examples of light outside the visible frequency band include near-infrared (NIR) light, infrared (IR) light, and ultraviolet (UV) light. Of course, other non-visible-light frequencies could possibly be used. However, the impact of such electromagnetic radiation (here, light) on the user must be considered. An important consideration for the particular wavelength(s) of light used is that the light needs to be reflected from the surface of the eye.

VTET sensor 104 includes a view-through region 108 and an active peripheral region 112 that at least partially surrounds the view-through region. VTET sensor 104 is designed to be placed relatively close to an eye 116 that is to be tracked. For example, the frontal distance, DF, from a front point, FP, on an eye to a plane, PL, containing active peripheral region 112 typically ranges from about 5 mm to about 25 mm. Since VTET sensor 104 is intended to be used in a setting where the user needs to see beyond the VTET sensor and since the VTET sensor is located close to eye 116 during use, at least a portion of the VTET sensor must be see-through to allow the user to view through the VTET sensor. This is a purpose of view-through region 108. In some embodiments that use reflected environmental light to effect eye-tracking, view-through region 108 also allows the environmental light to reach eye 116.

Active peripheral region 112 includes at least a first plurality of light-sensing regions 120. Each light-sensing region 120 is designed and configured to sense light reflected from eye 116 independently of each other light-sensing region 120 and may take any of a variety of forms. For example, in some embodiments, each light-sensing region 120 may be made up of one or more photodiodes, one or more LEDs (as light sensors), or light-sensing regions of a continuous light sensor that extends around the entirety or portion of active peripheral region 112, among others. Fundamentally and in general, there are no limitations on the structure and type of each light-sensing region 120 other than it be of an appropriate size and be able to sense the intensity of light reflected from eye 116 so as to effect tracking of movement of the eye.

In some embodiments, active peripheral region 112 is continuous around the entirety of view-through region 108. For example, when VTET sensor 104 uses visible light to effect eye tracking, it has been found that the first plurality of light-sensing regions 120 can be distributed, for example, evenly, in active peripheral region 112 360° around view-through region 108. However, when VTET sensor 104 uses NIR emitter to effect eye tracking, it has been observed that eyelashes reflect the NIR emitter fairly well, such that it can be desirable to not have any light-sensing regions 120 in the region of the VTET sensor adjacent to the upper eyelashes 116A of eye 116. In this case, active peripheral region 112 may be horseshoe shaped, for example.

As noted above, VTET sensor 104 is designed to be placed close to eye 116 during use. Consequently, the size of view-through region 108 may be relatively small. When view-through region 108 is circular in shape, the diameter, DVT, of the view-through region is typically on the order of about 3 cm to about 5 cm, although it can be of a different size or a different shape (e.g., oval, rectangle). In some embodiments, VTET sensor 104 may be attached to a lens 124 of a support structure 128, such as a lens of a pair of eyeglass frames, a lens of a virtual reality (VR) headset, or a lens of an augmented reality (AR) headset, among others. In some embodiments, VTET sensor 104 may be mounted separately from any lens that support structure 128 may have. For example, VTET sensor 104 may be mounted between lens 124 and eye 116. In some embodiments, support structure 128 may not include any lenses. In this case, VTET sensor 104 may be secured to support structure 128 so that it is proximate to the eye when VTET apparatus 100 is in use. As an example, VTET apparatus 100 may be part of a medical diagnosis device that comprises an eyeglass-like frame that has only a pair of VTET sensors 104 mounted thereto in place of eyeglass lenses.

In this connection, it is noted that while view-through region 108 is shown as being circular and active peripheral region 112 is shown as being annular, these shapes are not necessary. Indeed, the general shapes of view-through region 108 and active peripheral region 112 can be oblong, rectangular, or other shape. For example, a VTET sensor of the present disclosure, such as VTET sensor 104 of FIG. 1, can be adapted to a pair of eyeglass frames so that view-through region 108 and active peripheral region 112 conform to the shape of the eyeglass frames and corresponding lenses. It is also noted that active peripheral region 112 can be opaque or see-through. An opaque active peripheral region 112 may come about, for example, when the devices in the active peripheral region, such as the device (e.g., photodiodes) composing light-sensing regions 120, and their supporting circuitry (not shown) are opaque and mounted to an opaque circuit board. A see-through active peripheral region 112 may come about, for example, when the devices in the active peripheral region, such as the device (e.g., photodiodes) composing light-sensing regions 120, and their supporting circuitry (not shown) are fabricated using a see-through electronic device technology, such as an oxide technology (e.g., titanium oxide technology), among others. As an example, such devices and circuitry can be applied directly to a lens, such as lens 124.

Active peripheral region 112 may contain any suitable number of light-sensing regions 120. For coarse tracking, in some embodiments four sensing regions distributed evenly around active peripheral region 112 may be sufficient. However, higher tracking accuracy can be achieved with greater numbers of light-sensing regions 120. For example, some embodiments may include 8, 12, 16, 20, or more light-sensing regions 120. In some embodiments, from about 4 to about 144 individual light-sensing regions 120 may be provided; alternatively, from about 12 to about 96 light-sensing regions may be provided. In some embodiments, 4, 8, 16, or 32 individual light-sensing regions 120 may be provided. In some embodiments where it is desired to minimize power consumption, an analysis of power consumption versus accuracy can be performed to appropriately balance these considerations. In this connection, it is noted that in some embodiments, the number of light-sensing regions 120 being used can be changed from time to time to reduce power consumption. Active peripheral region 112 may have any suitable width, WP, needed to accommodate the light-sensing device(s) used for light-sensing regions 120 and the corresponding supporting circuitry. In an example, width WP is 10 mm or less. In another example, width WP is 5 mm or less.

As mentioned above, some embodiments of VTET sensor 104 rely on reflected environmental light to effect eye tracking. In such embodiments, it can be useful to improve accuracy of eye tracking using information, such as spatial and temporal intensity changes, about the light that is being reflected from eye 116 for effecting the tracking. For example, in some embodiments, the reverse side (inset of FIG. 1) of VTET sensor 104 is provided with a second plurality of light-sensing regions 132 that sense the intensity of environmental light coming toward eye 116 in real-time and in sync with first plurality of light-sensing regions 120 sensing the portions of that environmental light that is reflected from the eye. In some embodiments, each of light-sensing regions 132 is located in registration with a corresponding one of light-sensing regions 120 on the obverse side of VTET sensor 104. Each light-sensing region 132 may be of the same type as the corresponding light-sensing region 120 on the obverse side of VTET sensor 104. Environmental light may be from any suitable source, such as, but not limited to, one or more electronic display screens (e.g., for a VR, AR, or other type of interactive display, such as a display 136 of an interactive display device 140), among others.

While second plurality of light-sensing regions 132 can be provided for acquiring information about the environmental light, other means for obtaining that information can be used. For example, a camera 144 can be directed at display 136 of interactive display device 140 so as to obtain readings of time-varying intensity of light the display is emitting. As another example, interactive display device 140 may be in direct communication with VTET apparatus 100 via wired or wireless communication so as to provide frame-by-frame time-varying light-intensity information that the VTET apparatus can use to improve eye-tracking accuracy.

As also mentioned above, some embodiments of VTET sensor 104 rely on reflected light emanating from onboard the VTET sensor. In such embodiments, the obverse side of VTET sensor 104 may be provided with a plurality of light emitters 148 that emit the light that reflects from eye 116 and is used to effect the eye tracking. In one example, each light emitter 148 comprises one or more LEDs that emit NIR emitter that, because it is not visible to eye 116, does not disturb the user or interfere with the environmental light coming into the eye. When light emitters 148 are provided, they are typically distributed about active peripheral region 112 so as to provide good overall coverage of the front portion of eye 116. In some embodiments, each light emitter 148 is spatially separated from each other light emitter. In certain embodiments, each of the plurality of light emitters 148 emits an ultra-temporally-short, directional light beam from a complementary direction onto eye 116. In some such embodiments, each of the plurality of light emitters 148 sequentially emits an ultra-temporally-short, directional light beam from a complementary direction onto eye 116. By separating illumination from light emitters 148 in the time domain, for a given pupil position, separate spatial patters of reflected light under light rays coming in from different directions are obtained.

VTET apparatus 100 includes and may be controlled by one or more processors (collectively illustrated and referred to hereinafter as processor 152) via any suitable wired or wireless connection. Processor 152 may be any suitable processor, such as a microcontroller, microprocessor, an application specific integrated circuit, part of a system on a chip, or a field-programmable gate array, among other architectures. Processor 152 is configured to execute suitable machine-executable instructions 156 for controlling VTET apparatus 100 and processing algorithms, such as calibration algorithms and algorithms for tracking eye movement and handling eye blink, including any one or more of the algorithms described below in the detailed examples, among others. Machine-executable instructions 156 are stored in one or more memories (collectively illustrated and referred to hereinafter as memory 160), which may be any type(s) of suitable machine memory, such as cache, RAM, ROM, PROM, EPROM, and/or EEPROM, among others. Machine memory can also be another type of machine memory, such as a static or removable storage disk, static or removable solid-state memory, and/or any other type of persistent hardware-based memory. Fundamentally, there is no limitation on the type(s) of memory other than it be embodied in hardware. Machine-executable instructions 156 compose the software (e.g., firmware) of VTET apparatus 100. Processor 152 and memory 160 may be located in any suitable location, such as onboard support structure 128, offboard the support structure, or a combination of both onboard and offboard the support structure.

In some embodiments, it is desirable to minimize power consumption, especially for untethered devices incorporating a VTET apparatus of the present disclosure, such as VTET apparatus 100. This goal can be easy to achieve using principles of the present invention because of the relative low number of light-sensing regions needed and because ultra-low-power devices, such as microcontrollers, can be used. For example, in one of the examples described below, the VTET apparatus required only a credit-card size solar cell operating off of moderate ambient room lighting to power the VTET apparatus. Those skilled in the art will readily understand how to adapt VTET sensor 104 to a wide variety of applications, including the applications described below in detail in the following sections and logical variants thereof.

2. Eye Tracker without Active Emitters—Example Embodiment

This example is directed to a headset that includes a VTET sensor that does not include active emitters but instead uses environmental light as the basis for tracking movement of a user's eye. In an example instantiation, the headset is a VR headset of the mobile type in which one or more display screens are incorporated into the headset. The mobile headset is typically designed to exclude virtually all light except the light emitted from the onboard display screen(s). Other instantiations can include a VR headset for display screens that are located offboard of the headset. Generally, the principles are the same except that environmental light not emitted by the corresponding display screen(s), such as ambient light from room lighting and/or light from a window, may need to be considered depending on the presence, or not, of such light. For the sake of simplicity, the present example considers a headset in which the only light present and reaching the view-through eye-tracking sensor is from one or more display screens that display VR content.

A feature of eye movement critical to VR is "gaze tracking," i.e., determining a user's eye fixation direction. Not only does gaze tracking allow users to interact with the VR content just by glances, it also can greatly improve user's visual experience, reduce VR sickness, and save systems (display) energy. The energy saving can be achieved by foveated rendering, which progressively reduces image details outside the eye fixation region. Such energy saving is particularly beneficial for mobile VR headsets not having external power cords. In the present example, a low-cost, low-power-consumption gaze tracker is obtained using a VTET sensor that does not include any active emitters but rather reuses light from the VR screen(s) to track pupil location. By exploiting the fact that VR screen light is the sole and constant light source within the space of a VR headset to eliminate the need for active light emitters on the VTET sensor and by using a relatively small number of low-cost light-sensors, such as photodiodes, to sense screen light reflected from the exterior of a user's eye in certain directions, the VTET sensor can be made cost effectively and to have very low energy consumption.

2.1 Example Inner Structure of VR Headsets

Current VR headsets are classified into two types based on the head-mounted displays (HMDs): 1) tethered HMDs, displays built in the headset and connected to powerful desktop servers for rendering, and 2) mobile HMDs, which reuse screens of mobile phones slotted into the VR headset. Tethered HMDs typically offer better visual quality due to the computation power of external servers allowing more advanced rendering. However, they are constrained in mobility due to the need of tethered cords. Mobile VR, on the other hand, is self-contained offering full mobility, and yet suffers from relatively lower visual quality and limited battery life.

Figure 2A:
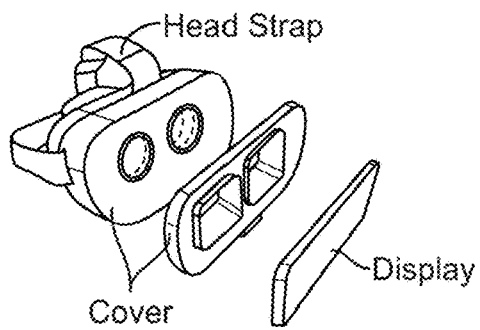
FIG. 2A is an isometric frontal exploded view of a conventional virtual reality (VR) headset.
Figure 2B:
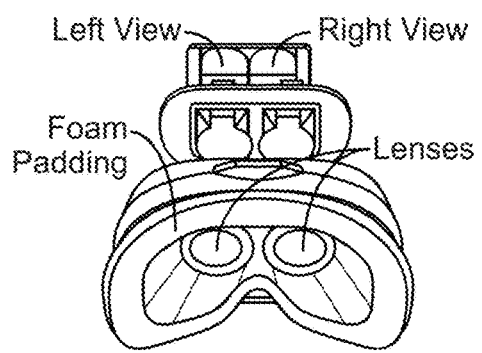
FIG. 2B is an isometric rear exploded view of the conventional VR headset of FIG. 2A.

Despite the differences in HMDs, VR headsets share a similar inner structure, with one or more display screens in the front and screen light passes through a pair of lenses (typically, 36 mm to 43 mm in diameter) positioned very closely (e.g., 1 cm to 2 cm) to eyes. The lenses divide the screen content into two slightly different 2D images tailored to the left and right eye. By angling the 2D images, the pair of lenses helps to create a 3D virtual scene perceived by the user. FIGS. 2A and 2B show main components of an example mobile VR headset. Foam padding and a head strap block ambient light from entering the headset to create an immersive virtual scene. They also improve the comfort of wearing the headset.

2.2 The Light Absorption Effect

A VTET-sensor-based apparatus of the present disclosure leverages the light-absorption effect of the pupil when the observation point is not right next to the illumination source.

Figure 3:
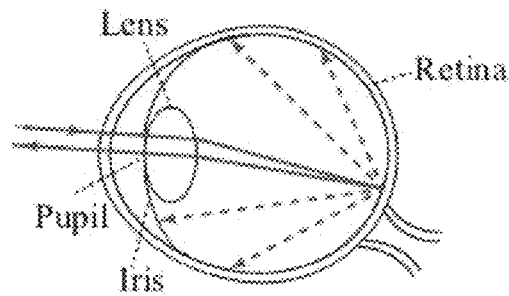
FIG. 3 is a cross-sectional view of an eye showing light entering the pupil being absorbed directly or after diffuse reflection at the retina.

In essence, the pupil is a hole in the center of an iris, which allows light rays to enter the retina. For an observation point off the axis of the illumination's optical path, light rays entering the pupil are absorbed either directly by the eye's inner tissue, or after diffuse reflections at the retina by missing the exit from the pupil (FIG. 3). The light reflected by the retina can only be sensed if the observation point aligns with the optical path of the illumination source, since the eye acts as a retro-reflector. A photodiode also perceives light diffused by other regions of the eyeball. However, the intensity of diffused light from other regions is negligible. The pupil's light absorption explains the dark pupil effect exploited by prior eye tracking methods, where a camera is placed off the optical axis of the light source to observe the dark pupil.

Figure 4:
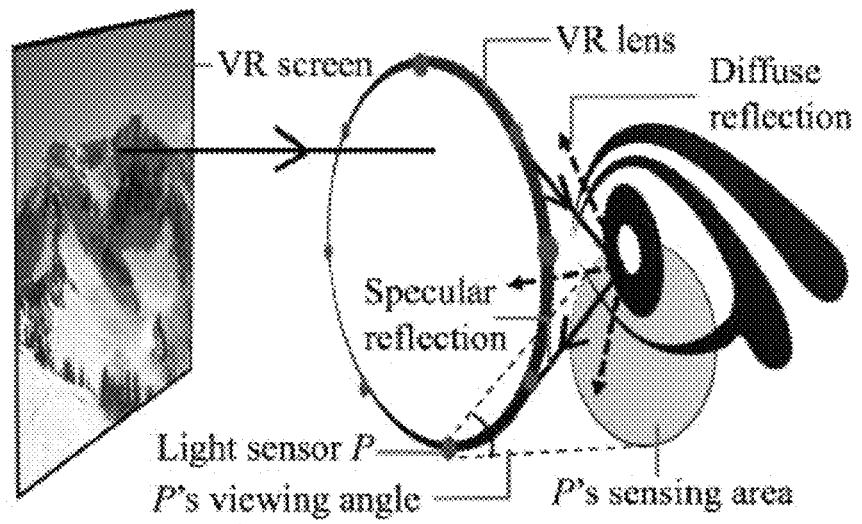
FIG. 4 is a diagram illustrating a light-sensor on a VR lens boarder sensing light reflected by a region of an eye.

In the VR context, the pupil's light absorption influences reflected screen light observed by photodiodes on the boundary of each VR lens (FIG. 4). Here screen light passes through a VR lens, strikes an eyeball, and is reflected. Light-sensing regions (i.e., observation points), here, photodiodes, are placed to avoid obstructing the lens and thus off the axis of screen light. Each photodiode perceives reflected light rays within its viewing angle. Because of its short distance (e.g., 1 cm) to the eye and limited viewing angle (e.g., ±45°), a photodiode perceives light reflected by only a region of the eyeball. Take the bottom photodiode P (FIG. 4) as an example, it senses screen light reflected by the bottom region of the eyeball. As a result, when the pupil moves to the bottom, photodiode P perceives a larger decrease in reflected light because of the pupil's light absorption; when the pupil moves to other regions, photodiodes close to those regions perceive larger decrease in reflected light.

Figure 5:
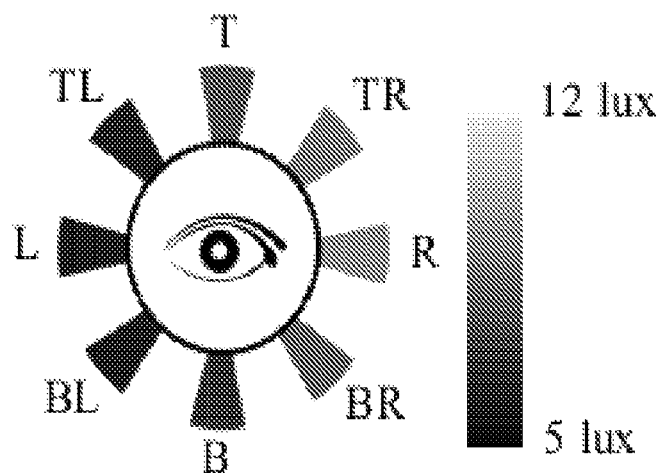
FIG. 5 is a diagram illustrating reflected light intensity at 8 photodiodes in close proximity to an eye.

To examine this phenomenon in practice, experiments were conducted using low-cost photodiodes and a mobile VR headset with a mobile phone providing the VR display. A ring-shaped printed circuit board (PCB) hosting eight photodiodes and their circuits was fabricated for the VTET sensor. The PCB was narrow (2 mm) with a diameter matching the VR lens to avoid affecting the user's viewing of VR content. On the PCB, photodiodes were spread out evenly, sensing reflected light in the top (T), bottom (B), left (L), right (R), top-left (TL), top-right (TR), bottom-left (BL), and bottom-right (BR) directions around the eye. Each photodiode had a built-in analog-to-digital converter (ADC) that outputted light intensity readings at 10 Hz. The photodiodes were connected to a microcontroller to collect sensor data. Answers to the following questions were sought:

Question 1: Can reflected screen light be sensed by light sensors? In the experiments, the starting point was to examine whether low-cost photodiodes can sense screen light reflected by eyes and capture the pupil's light-absorption effect. In the experiment, a participant wore the headset with the PCB attached to the left VR lens. The intensity of screen light was measured as 100 lux at the lens. The participant was first instructed to stare at a center dot on the screen for 3 seconds while data was collected from photodiodes. Each photodiode's readings was averaged; the results are plotted in FIG. 5. In FIG. 5, the darkness of a bar indicates the light intensity perceived at this location. From the results, two observations were made. First, despite being 90%+ weaker than incoming screen light, reflected screen light can be reliably measured by photodiodes. It is far above the minimal intensity (0.01 lux) that the photodiode can sense. Also, sensor readings are very stable, with the standard deviation of 0.02 lux. Second, the reflected light is non-uniform across photodiodes, even under uniform screen light. It was hypothesized that this is due to the asymmetry of the eye structure and its surrounding area, where reflectivity differs across directions.

Figure 6:
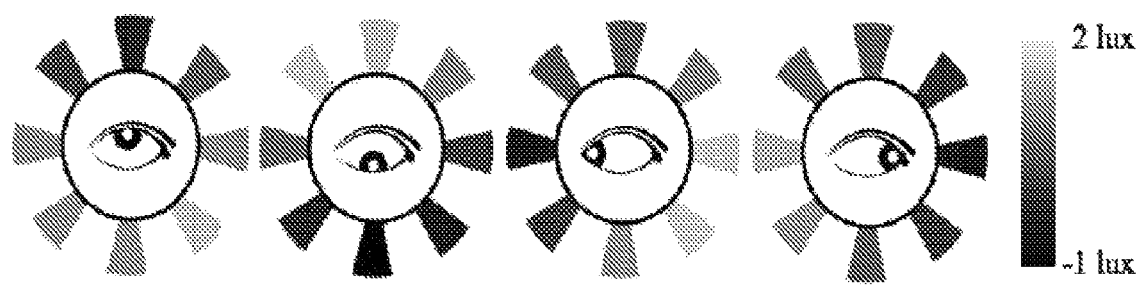
FIG. 6 is a series of 4 diagrams illustrating reflected light intensity at 8 photodiodes in close proximity to an eye for 4 differing pupil positions showing how pupil position affects reflected light intensity.

The participants were then instructed to stare at four dots (top, bottom, left, and right) on the screen, each for 3 seconds. To examine whether photodiode can sense the pupil's light-absorption effect, the change of reflected light intensity observed by each photodiode were examined by subtracting its reading under a center pupil (FIG. 5). As shown in FIG. 6, photodiodes in the pupil's direction perceived larger decrease in light intensity (i.e., darker bars) as the pupil absorbs more light, while photodiodes in the opposite direction perceived stronger reflected light as the pupil's light absorption has less impact. The result demonstrates that photodiodes can capture the subtle reflected light change caused by the pupil's light absorption.

Next, the brightness of the white screen was varied and the above experiment was repeated, seeking to understand the minimal level of screen light that allows photodiodes to sense reflected light reliably. From the experiments, it was observed that if the screen light is above 10 lux after passing the VR lens, then the reflected screen light is above sensor's noise range (0.05 lux) and thus can be reliably measured. It was further examined whether the 10-lux threshold can be met by existing VR screen content. Twenty popular VR applications supported by either mobile or tethered HMDs were tested. A photodiode was placed at the back of the VR lens facing the VR display to measure the screen light intensity after passing the lens. The experiment was conducted in a dark room so that screen light is the only light source. It was seen that 99% of screen content led to screen light above 15 lux, demonstrating that screen light of most VR content is sufficiently bright to be reused for detecting gaze direction.

Question 2: Would ambient light interfere with the sensing of reflected screen light? Another natural question is whether ambient light can leak in the VR headset and interfere with the sensing of weak reflected screen light. To examine the impact of ambient light, a light sensor was placed on each VR lens and the display within a VR headset was turned off. A participant was then asked to wear the headset under normal office lighting (400 lux), and light sensor readings were recorded from the light sensor. This experiment was repeated using five popular VR headsets in the market, including headsets of both mobile and tethered HMDs. Table 1, below, shows the mean and standard deviation of sensor reading for each headset. It is seen that for all headsets except headset H5, light intensity within the headset is zero, demonstrating that the foam padding and head strap of these headsets effectively blocked ambient light from entering headsets and screen light from the display was the only light source for those headsets. Headset H5, on the other hand, had neither foam padding nor head strap, letting a slight amount of ambient light rays enter the headset. However, the intensity of the leaking ambient light is only 0.2 lux, similar to sensor's noise level, and thus its impact was negligible.

TABLE 1

| VR Headset | | H1 | H2 | H3 | H4 | H5 |
|---|---|---|---|---|---|---|
| Sensor Data | Mean | 0 lux | 0 lux | 0 lux | 0 lux | 0.2 lux |
| | Std | 0 lux | 0 lux | 0 lux | 0 lux | 0.1 lux |

Figure 7:
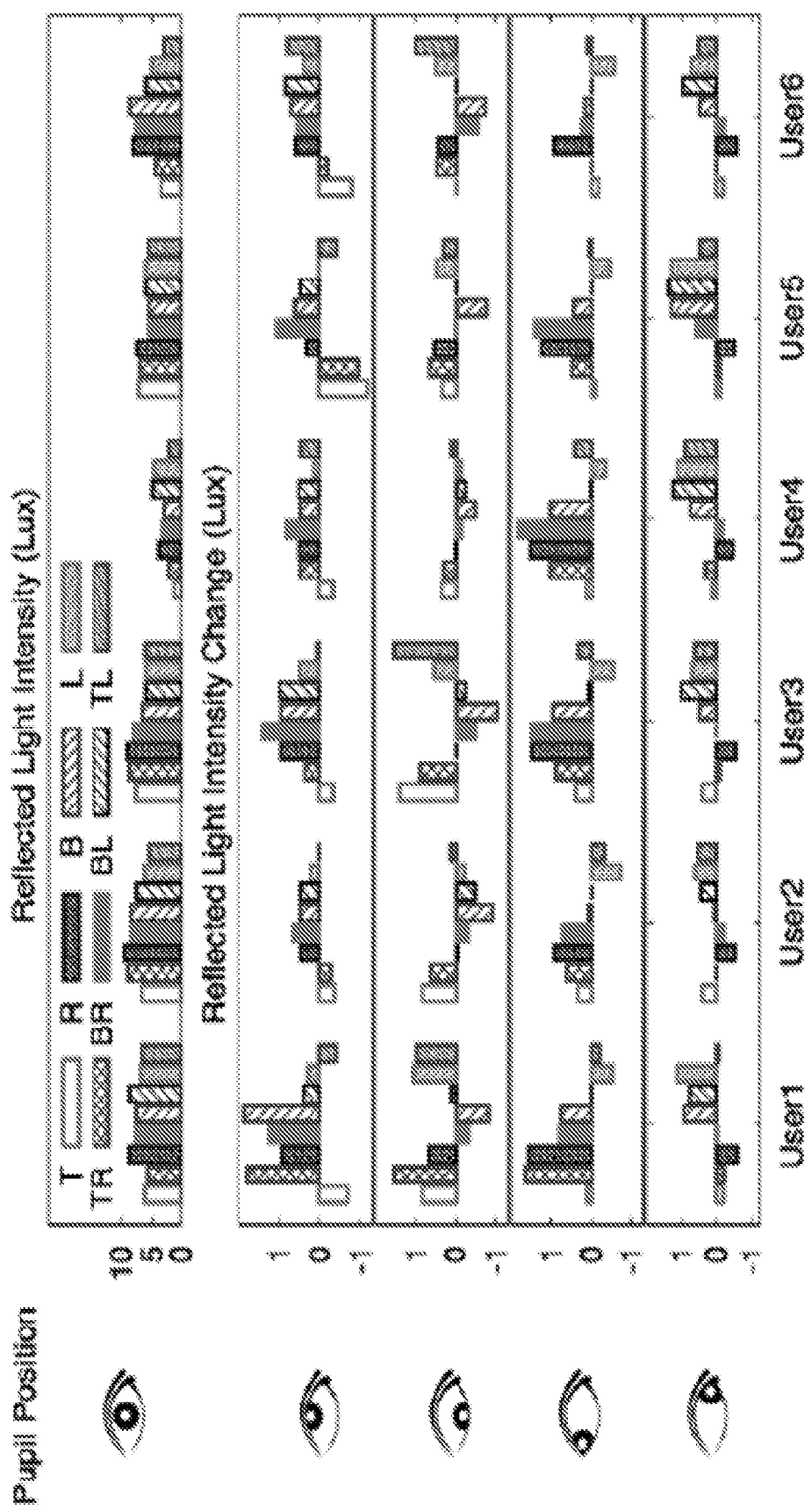
FIG. 7 contains 5 sets of graphs of light intensities at 8 photodiodes when the pupil is in 5 different positions showing how pupil position affects reflected light intensity.

Question 3: Is it a universal phenomenon across users? The experiments were repeated with different users, aiming to understand whether the pupil's light-absorption effect can be observed across users with different eye characteristics. Six participants (Table 2, below) of ages ranging from 18 to 33 years old were invited. Their eyes varied in color (green, black, blue), size, and length of eyelashes. Two participants wore contact lenses. Their skin color also differed (white, yellow, black). Each participant was asked to wear the VR headset containing the VTET sensor and the prior experiment in FIG. 5 was repeated. FIG. 7 plots the reflected light intensity at each photodiode when a participant stared at screen center. It was observed that the absolute reflected light intensity differed across users, indicating that eye characteristics affect light reflection. In particular, for the participant with darker skin (User 4), the reflected light was lower than other users with lighter skin colors. This was likely because some light rays are reflected by the skin around the eye and dark skin has lower reflectivity.

TABLE 2

| User ID | 1 | 2 | 3 | 4 | 5 | 6 |
|---|---|---|---|---|---|---|
| Eye Color | Blue | Black | Black | Black | Green | Black |
| Skin Color | White | Yellow | Yellow | Black | White | White |
| w/Contact Lenses | No | Yes | No | No | No | Yes |

The change in reflected light when the pupil moves to the other direction was then examined. For each other gaze direction, FIG. 7 (bottom) plots reflected light observed by each photodiode, minus its reading under a center pupil. It was observed that despite the differences in absolute light change, the pupil's light absorption effect was consistently observed across users. For instance, when the pupil moves to the top, the top photodiode observed a decrease in reflected light intensity for all users; when the pupil is on the left, the left photodiode similarly observed a drop in reflected light intensity across all users. The results indicate the pupil's light absorption effect can be consistently observed across users. On the other hand, the results also indicate challenges in dealing with diverse eye and skin characteristics, which are elaborated on below.

In summary, the experiment results confirmed the feasibility of using low-cost photodiodes around VR lens to sense the pupil's light-absorption effect. Under static screen light, this effect results into a spatial pattern of changes in photodiode readings correlated to the pupil movement and can be exploited to infer gaze direction.

2.3 Challenges

To exploit the pupil's light absorption property for VR gaze tracking, several challenges must be faced. The first challenge comes from screen light dynamics. Prior experiments assume uniform, static screen light to illustrate the concept. However, actual VR screen content is colorful and dynamic, which emits screen light varying both spatially and temporally. As a result, the reflected light perceived by photodiodes also inherently varies spatially and temporally, even under a fixed pupil position. The spatial variation makes it hard to estimate the reflected light when the pupil is in the center, given that the asymmetric eye structure also affects reflected light intensity in a non-uniform manner (FIG. 5). The temporal variation of screen light makes it infeasible to leverage prior observations for inferring non-uniform reflected light. Therefore, the spatial pattern of reflected light changes is no longer an effective indicator of pupil position. Furthermore, reflected light intensity varies from 0.5 lux to 5.5 lux even without any pupil movement, while the reflected light change caused by pupil movement is within 2 lux (FIGS. 6 and 7). Thus, the challenge lies in extracting the reflected light change related to pupil movement given screen light dynamics.

A second challenge is to derive a gaze vector based on the light absorption effect while handling diverse eye and skin characteristics across users. A recent study has revealed that user diversity contributes the most to eye tracking errors. Similarly in the present context, user diversity makes it hard to predict the reflected light under a center pupil, as shown in FIG. 7 (top). Even if the change in reflected light with respect to that under a center pupil can be derived, its relation to the actual gaze vector can slightly vary across users. Simply seeking the photodiode with the largest decrease in reflected light leads to a very coarse estimate of gaze direction, with error$\approx 360°/N$, where N is the number of photodiodes.

Additionally, blink is another factor that can interfere with the sensing of reflected light intensity. In addition, in some embodiments it is desired that the gaze tracking algorithm used needs to entail low computational overhead so that the system can infer gaze direction in real time with low power.

2.4 Example VTET Sensor System Overview

At high level, a VTET sensor system of the present disclosure can address the above challenges. To deal with non-uniform, time-varying screen light, the present example VTET sensor system uses an additional set of photodiodes facing the VR display to sense incoming screen light in differing directions. Based on the sensed screen light, the example VTET sensor system estimates the reflected screen light assuming the pupil is in the center and extracts features related to the pupil's light-absorbing effect. These features are used to infer gaze vectors in real time using supervised learning. To deal with user diversity, the example VTET sensor system leverages a quick calibration to customize the model for estimating reflected light and parameters in the trained learning model. The example VTET sensor system also runs a parallel process that detects the blink event by examining photodiode data over a time window. The following elaborates on an example VTET sensor system design and system flow.

Figure 11A:
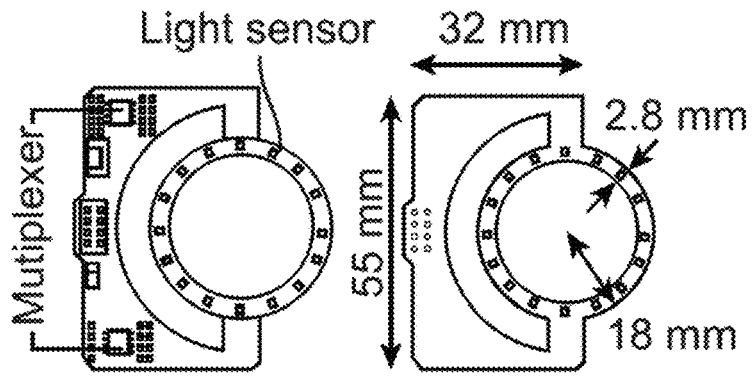
FIG. 11A contains front-side and back-side elevational views of an example instantiation of a VTET sensor.

Sensor Platform. The design of the present example VTET sensor system relies on a dual-side light-sensing unit, where photodiodes are embedded in both sides in a back-to-back manner (see FIG. 11A). The sensing unit is realized as a thin, ring-shaped (annulus) PCB and easily attached to the back of either VR lens (one for each VR lens). Photodiodes on one side (reverse side) of the PCB face the VR display and sense incoming screen light in different directions, while photodiodes on the other side (obverse side) of the PCB face user's eyes and sense screen light reflected by the eyeball. Because of the small form factor of the photodiode, the PCB, which is in the peripheral region of the VTET sensor, can be made in a very narrow width (e.g., 2 mm) to ensure that it does not obstruct user's view through the view-through region. A user study to examine the impact of our sensing panel on user's perception is described below.

Figure 8:
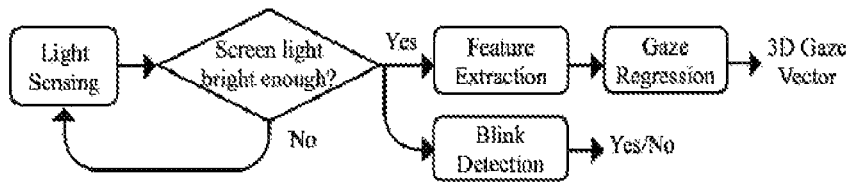
FIG. 8 is a flow diagram illustrating an example method of determining a 3D gaze vector and simultaneously detecting eye blink.

System Flow. The present example VTET sensor system starts with a short (e.g., 3-minute) calibration to calibrate system parameters. FIG. 8 shows an example system flow after calibration. The example VTET sensor system first checks whether the sensed incoming screen light is sufficiently strong (i.e., above 10 lux in our experiments) for later gaze tracking. If so, the example VTET sensor system starts two parallel processes, one for inferring the 3D gaze vector, and the other for detecting blink. Specifically, the gaze tracking process comprises three steps:

1) estimating the reflected light under a center pupil; 2) extracting features on the reflected light change associated with pupil position, and 3) running a boosted tree regression algorithm to estimate a 3D gaze vector. The blink detection process examines the reflected light changes and leverages the spatial correlation among changes perceived by photodiodes to detect blink. Since a blink typically lasts 300 to 400 milliseconds, in this example the VTET sensor system runs the blink detection algorithm every 0.3 seconds.

2.4.1 Design

Based on the real-time photodiode data, the example VTET sensor system infers 3D gaze vectors represented as normalized 3D vectors. The following first introduces estimating reflected screen light under a center pupil and then describes an example learning algorithm for gaze inference and the mechanism for blink detection.

2.4.1.1 Estimating Reflected Screen Light

Given N photodiodes on each side of the annulus sensing panel, it is sought to model the relationship between screen light sensed by N front photodiodes (facing the screen) and the reflected screen light sensed by N back photodiodes (facing the eye), given a fixed pupil location (center). This relationship characterizes the impact of the reflections that occur after screen light rays strike the eyeball.

Experiments. The annulus PCB in FIG. 11A was attached to a wearable VR headset. A user was asked to wear the headset and to stare at screen center. Two-hundred fifty seven images were displayed on the screen to generate non-uniform, time-varying screen light and to collect data from all photodiodes. For every pair of front and back photodiodes, the Pearson correlation coefficient was calculated. This is the standard measure of the linear correlation between two variables, with r ($-1 \leq r \leq 1$) indicating the strength and direction of the correlation, and p indicating the significance of the finding.

Table 3, in FIG. 31, lists the correlation coefficients (r-values, $p<0.01$) for all pairs. It is noted that T, R, B, and L denote top, right, bottom, and left directions, respectively. Interestingly, a strong linear correlation commonly exists between back photodiode in direction d and front photodiode in direction d' that is diagonally opposite to d. Front photodiodes in directions other than d' are also correlated with back sensor in direction d, and the correlation becomes weaker for front photodiodes further away from direction d'. Take the top-right (TR) back photodiode as an example, its perceived reflected light has the strongest linear correlation ($r=0.91$) with that at the bottom-left (BL) front photodiode. For front photodiodes further away from BL, the correlation gradually decreases. This observation suggests that reflected light intensity is dominated by specular reflections (possibly due to eyeball's glossy surface), which direct each incoming screen light ray to a coplanar direction diagonally opposite to its incident direction. Diffuse reflections, on the other hand, scatter a light ray in a broad range of directions. Although they also contribute to the reflected light intensity perceived by a back photodiode, diffused light rays are much weaker and thus play a much less significant role.

Given the linearity of light transport (i.e., contributions of individual light rays add up at a receiver location), it was considered to model the relationship between back and front photodiodes' readings as a simple linear relation. Similar linear models have been applied in prior works in computer graphics and vision. Specifically, let I be the vector of N front photodiodes' readings. Assuming a center pupil, the estimated back photodiodes' readings, denoted as vector $\tilde{\mathcal{R}}$, can be written as:

$$\tilde{\mathcal{R}} = W \cdot I \quad (1)$$

where W is a N×N weight matrix: $W=\{w_{ij}|i,j\in[1,N]\}$. $w_{ij}$ indicates the contribution of incoming light intensity Ij perceived by front photodiode j to the estimated reflected light $\tilde{\mathcal{R}}_i$ perceived by back photodiode i.

Calibration. The weight matrix W can differ across users based on their eye and skin characteristics (FIG. 7). Subtle offset of the headset to the eyes can also affect the screen light's reflections and thus W. To deal with user diversity and headset offsets, W is determined in a calibration phase when a user first put on the VR headset. During the calibration, the user watches a short video while staring at the screen center. In the meantime, the readings of all front and back photodiodes are then used to calculate W using linear regression. Specifically, let R be the vector of measured back photodiodes' readings, we are seeking W that leads to the estimated vector best matching the measurement R:

$$\overline{W} = \underset{W'}{\operatorname{arg\,min}} \|\mathcal{R} - \tilde{\mathcal{R}}(W')\|^2 \quad (2)$$

With the calibrated W, upon real-time readings I from front photo-diodes, we can then estimate on the fly reflected light at each back photodiode using Eq. (1), assuming the pupil is in the center.

To shorten the calibration, the video content was judiciously designed so that it best represents the variety of brightness distribution of the screen using a limited number of frames. Specifically, each video frame was divided into 10×10 grids and the gray-scale color of each grid was randomly changed based on a quasi-random sampling strategy in the color space. Quasi-random sampling can generate samples in high-dimensional space more uniformly than the traditional pseudo-random sampling. This strategy allows for the use of a 2-minute to 4-minute video to estimate W accurately.

2.4.1.2 Gaze Inference

The next step of the example VTET sensor system is to extract features related to pupil position and infer a 3D gaze vector. Given incoming screen light, the model in Section 2.4.1.1, above, estimates the reflected light that each back photodiode would perceive if the pupil is in the center. Thus, the difference between this estimate and the measured reflected light is caused by the offset between the actual pupil position and the center. Specifically, the normalized change is considered, since the actual amount of change in reflected light can depend on the level of reflected light intensity. Hence, let $R=\{R_1, \ldots, R_N\}$ denote the vector of measured reflected light at N back photodiodes, $f_i = R_i/\tilde{R}_i$ is computed for each photodiode, and the resulting set $\mathcal{F} = \{f_1, \ldots, f_N\}$ is used as the feature vector for later gaze inference.

In the present example, gaze is estimated using supervised learning. In the present instantiation, boosted trees (or tree ensemble), which represent the relationship between features and prediction values as a set of regression trees, was chosen. Here, each tree is similar to a decision tree but differs in that it associates a weight to each leaf (i.e., decision). By summing the predictions of multiple trees, boosted trees improve the reliability and accuracy of the final prediction. Another benefit is its lightweight computation. Once the tree ensemble is trained, online regression involves only comparison operations. Thus, it is fast and entails low power, which can be important for real-time execution on microcontrollers. Other options, such as Support Vector Machine (SVM) and its variants (SVC1V1, SVOREX, REDSVM), and feed-forward neural network could alternatively be used. However, those algorithms entail either higher latencies or larger memory footprints. For example, neural network involves floating-point addition, multiplication, and exponential operations; SVM and its variants require storing a large number of support vectors (e.g., 10K vectors for a training set with 200K samples).

Figure 9:
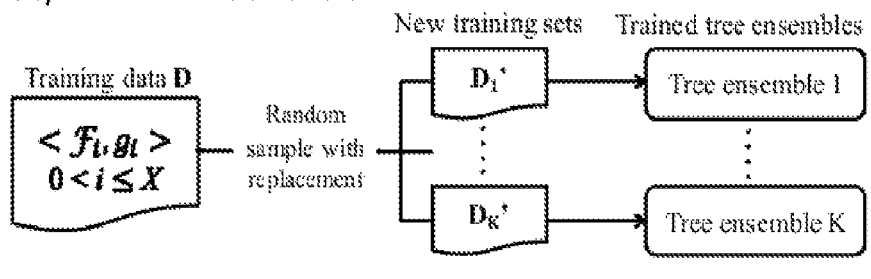
FIG. 9 illustrates a two-step process of applying bootstrap aggregating over boosted trees, where K tree ensembles are trained using training sets generated by random sampling with replacements, and their optimal linear combination is derived by linear regression with additional training samples.
Figure 9:
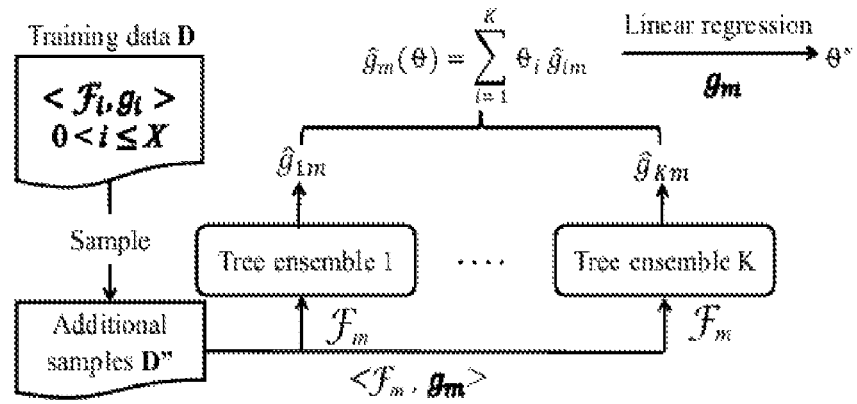

Offline Training. In the present instantiation, the boosted trees offline are trained using a data set consisting of computed feature vectors and 3D gaze vectors from existing eye trackers. Let D denote the training set with size X, where D consists of X pairs of feature vector and actual 3D gaze vector g, i.e., D={$<\bar{\mathcal{F}}_i, g_i>|0<i\leq X$}. To improve the stability and accuracy of the inference, the power of multiple tree ensembles are combined by applying bootstrap aggregating (i.e., bagging). As illustrated in FIG. 9, this has two steps. First, K tree ensembles are trained using K new training sets generated from the original training set D. Each new training set $D'_k$ (with size X') is created by uniformly sampling D with replacement. Each new training set is then used to train a tree ensemble separately. Second, the resulting K tree ensembles are combined linearly. Additional training samples are used to seek the optimal linear combination using linear regression. Specifically, for each training sample <F, g>, it is fed to each tree ensemble to obtain the prediction value. Let $\hat{g}_j$ be the prediction from the j-th tree ensemble, then the final prediction $\hat{g}$ is derived as $\hat{g}(\theta) = \Sigma_{j=1}^{K} \theta_j \cdot \hat{g}_j$, where $\theta_j$ is the weight of the j-th tree ensemble. A linear regression is then run to determine the optimal $\theta^*$, such that $\theta^* = argmin_\theta \|\hat{g}(\theta) - g\|$. By combining multiple tree ensembles, bootstrap aggregating seeks to learn underlying correlations that could differ across user groups.

Online Inference. With the trained tree ensembles, the present example VTET sensor system's online inference operates with only photodiode data coming on the fly. Since an individual user can have his/her own features and differ from users in the training data, to better address user diversity, for each user during online testing, $\theta^*$ is calibrated through a short (e.g., 1-minute in the experiments) calibration phase (after the phase of calibrating W). It is a simple game where the user is prompted to stare at various dots with known locations spread in a virtual scene. The front and back photodiodes' readings are then fed into the K trained tree ensembles to obtain predicted $\hat{g}$. Assuming the dots are the actual locations the user stares at, gaze vectors g are calculated based on actual dot locations and treat them as ground truth. Using linear regression, the optimal adjustment are computed over existing $\theta^*$, so that ($\theta^*+\epsilon$) best matches this user's ground truth. Specifically, $\epsilon$ is calculated as:

$$\epsilon = \underset{\epsilon'}{argmin}(\|\hat{g}(\theta^* + \epsilon') - g\|^2 + \lambda\|\epsilon'\|^2) \quad (3)$$

where $\lambda$ is a regularization term to constrain the amount of adjustment $\epsilon$. $\lambda$ is determined using cross-validation among users in the training data set. Slight adjustment over $\theta^*$ are considered, rather than calculating a new $\theta^*$, because of the small amount of data from the short calibration phase. Overall, this short calibration allows the system to slightly adjust $\theta^*$ to best fit a specific user.

After the quick calibration, upon each set of back and front photodiode readings coming on the fly, the 3D gaze vector is inferred as follows: 1) with front sensors' readings I={$I_1, \ldots, I_N$}, $\tilde{R}_i$, the reflected light under a center pupil for each back photodiode i based on Eq. (1), is estimated; 2) based on back sensors' readings R={$R_1, \ldots, R_N$}, the feature vector F={$f_i$}, where $f_i = R_i/\tilde{R}_i$; 3) is derived; 3) F is input into each of the K trained tree ensemble and obtain prediction $\hat{g}_j$ from tree ensemble j; and 4) the gaze vector is inferred as $\hat{g}(\theta^*+\epsilon) = \Sigma_{j=1}^{K}(\theta^*+\epsilon_j) \cdot \hat{g}_j$.

2.4.1.3 Blink Detection

Figure 10:
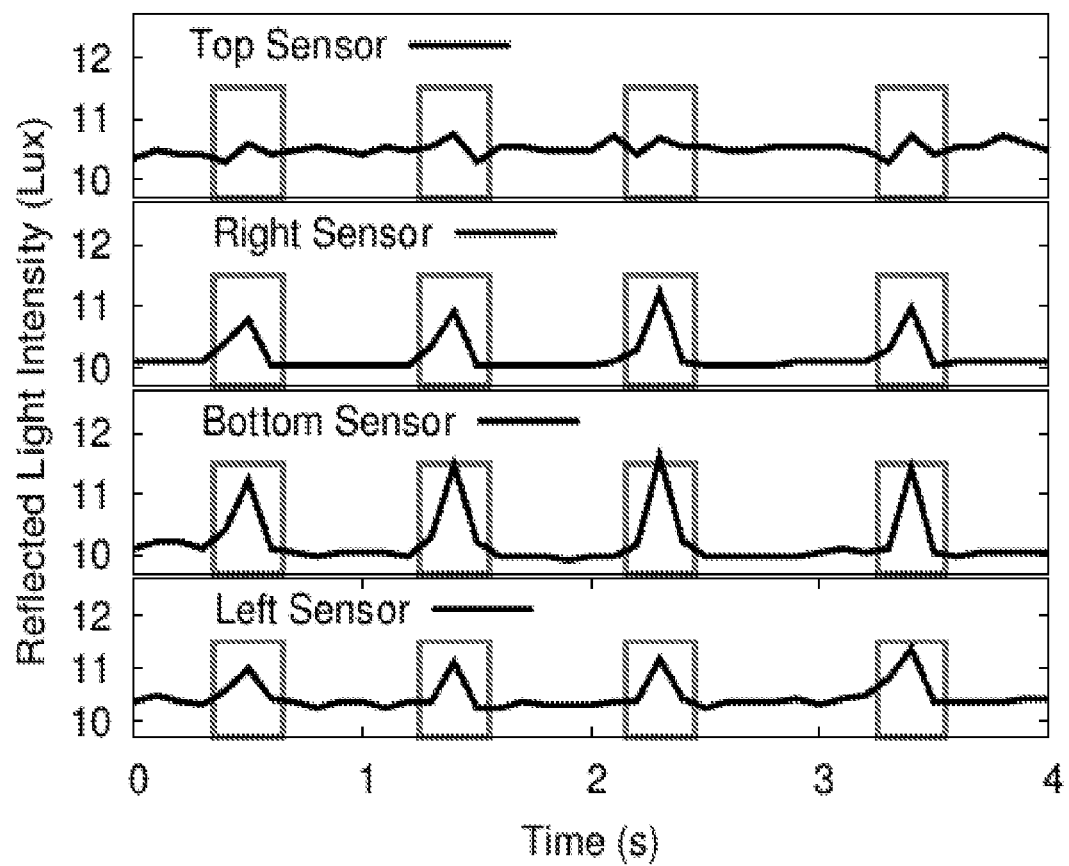
FIG. 10 is a diagram illustrating reflected light intensity changes when a user blinks an eye, wherein each box represents a blinking instance.

The present example VTET sensor system detects a blink event based on a simple observation: when a blink occurs, the reflected light intensity around the eye experiences similar pulse changes in most directions. FIG. 10 shows the time series of reflected light intensity perceived by four photodiodes around the eye. It has been observed that reflected light intensity in three directions exhibit similar pulse changes during a blink. When the eye is closed, the pupil is covered by the eyelid, which reflects light rays better than the pupil. When the eye is opened, the pupil continues absorbing incoming light rays, which decreases the reflected light intensity around the eye. Since the eyelash can block some light rays between the eyeball and photodiodes, this pulse change is not significant at the top photodiode. However, a blink still leads to noticeable patterns in most photodiodes. Thus, by counting the number of photodiodes concurrently perceiving pulses of reflected light intensity, the occurrence of a blink can be detected.

To detect the reflected light pulses around the eye, gaze features are first extracted to remove the impact of screen content change using the estimate of reflected screen light (Section 2.4.1), above. Then, the first-order derivatives of time series of gaze features is computed at each photodiode. A pulse of light intensity can be detected when two adjacent first-order derivatives are positive and negative, respectively. When a sufficient number (half of the photodiodes in our implementation) of photodiodes perceive pulses in their gaze features, the example VTET sensor system outputs a blink event. To further reduce the false positive due to subtle screen content change (e.g., cut scene in movie), the example VTET sensor system bypasses the blink detection when half of the front photodiodes concurrently detect a pulse in incoming screen light.

2.5 Prototype

A prototype of the example VTET sensor system was built using off-the-shelf hardware, and it was attached to an existing VR headset. The prototype contained three main components:

Light-Sensing VTET sensor. A thin (0.8 mm), ring-shaped PCB was fabricated that hosted 16 photodiodes on each side and their associated circuits (e.g., resistors, capacitors). Each photodiode was 1.9 mm×1.25 mm in size, so the PCB ring, and the peripheral active region of the VTET sensor, could be narrow in width (2 mm) to avoid affecting the user's view through the view-through region of the VTET sensor. The ring diameter was 36 mm, customized to fit the lens of the headset used.

The particular type of photodiode was selected for three reasons. First, it is ultra-low power, consuming only 6 µW in the active state. Also, with a built-in analog-to-digital converter (ADC), it directly outputted digitized light intensity (in lux, at 10-Hz rate), thus removing the need to add external ADC that can be energy-consuming. Second, as an ambient light sensor responding only to visible light (400 nm-700 nm), it can sense very weak light (as low as 0.05 lux) and provides a high resolution (0.01 lux). Thus, it is suitable for sensing weak reflected light in the present scenario. Third, it has a ±45° field of view (FoV). With only 1.8 cm to the eye, this FoV is sufficient for covering the whole eye surface after aggregating the coverage of 16 photodiodes.

Photodiodes transmit raw data to a microcontroller through a hardware Inter-Integrated Circuit (I2C) interface at a clock rate of 400 kHz. Given that the selected photodiode type allowed up to 4 serial bus addresses, one hardware I2C can only differentiate up to 4 photodiodes. To support fetching data from 32 (16 front and 16 back) photodiodes, a switch was designed using two 4-channel analog multiplexers (74HC4052). The switch divided 32 photodiodes into 8 groups and let each group transmit data to the microcontroller in turn. In the experiments, the switch consumed less than 2 µW, and the hardware I2C interface was 1.5 times more energy-efficient than software simulation I2C interface for supporting the 32 sensors. The switch and its associated circuit were integrated into a side PCB board connecting to the PCB ring. This was a different setup from the PCB used in our prior experiments (FIG. 5), which was a single-sided PCB ring hosting eight photodiodes. This new PCB design led to a cleaner look with only 7 wires connecting to the microcontroller. An arc gap allowed the rim of the VR lens to fit in.

Microcontroller. The microcontroller periodically woke up to receive data from photodiodes, computed the feature vector related to pupil position, and ran the gaze inference algorithm (see Section 2.4.1.2, above) to derive a current 3D gaze vector. A particular microcontroller was chosen because of its ultra-low power according to the power benchmark ULPBench. ULPBench is from the embedded microprocessor benchmark consortium (EEMBC) and is a standard way to compare power performance on microcontrollers. The gaze inference results can be either stored on the microcontroller or transmitted to other computing units through a USB cable.

Energy-Harvesting Unit. To demonstrate the example prototype's ultra-low power, a credit-card sized solar cell was added atop the headset to harvest energy from indoor lighting to power the entire system (sensing and computation). The solar cell selected was an amorphous silicon solar cell and was sensitive only to visible light (wavelengths from 400 nm to 700 nm). Therefore, it was ideal for harvesting indoor light. A buck-boost DC/DC converter was used to maintain the output voltage at 4V, which maximized the output power at varying light conditions (e.g., 200 lux-800 lux).

Figure 11B:
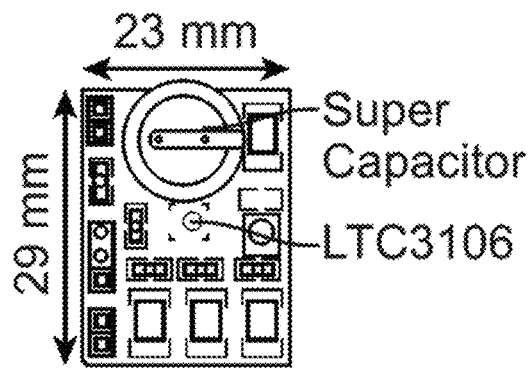
FIG. 11B is a front-side view of an example instantiation of an energy harvesting unit of a VTET apparatus.

The main challenge in designing the prototype system unit was to maintain an output power above the minimum required by the system. Since the solar cell was atop the headset, user's head movement could cause drastic variations in light intensity perceived by the solar cell, resulting into drastic changes in output power (200 µW to 1200 µW). Such power variation can make the system run out of power occasionally. To address this problem, a 15-F super capacitor was used to store extra harvested energy (FIG. 11B). The capacitor could be fully charged after 12 hours under 600-lux lighting. Once fully charged, it could support the prototype system for 18 hours without harvesting additional energy. It allowed the prototype system to run in a dark environment and to deal with sudden light changes due to head movement.

2.6 Experiments with Prototype

To evaluate the prototype described in Section 2.5, above, 30 participants (from 18 to 45 years old, 19 males and 11 females) were recruited. The user information is summarized in Table 4, below. Three out of 30 participants wore contact lens. The first focus was on gaze tracking performance across participants and dynamic VR content. Then, the prototype's energy consumption was measured and the tradeoff between energy and performance was analyzed. In addition, several practical factors when using the prototype were considered, including head movement and user perception.

TABLE 4

| | Eye Color | | | Skin Color | | |
|---|---|---|---|---|---|---|
| | Black | Blue | Green | White | Yellow | Black |
| # of Users | 18 | 8 | 4 | 15 | 9 | 6 |

Experimental Setup. The prototype VTET sensor system was added to an existing VR headset already equipped with an original equipment manufacturer (OEM) eye-tracking system that provided 3D gaze vectors at 120 Hz with a claimed accuracy of 1° error. The prototype VTET sensor system was run concurrently with OEM eye-tracking system and used the OEM eye-tracking system's output as ground truth to evaluate the performance of the prototype VTET sensor system. The OEM eye-tracking system used near-infrared emitters and infrared cameras in the headset to track gaze. Since the light sensors in the prototype VTET sensor system only respond to visible light (400-700 nm) spectrum, the OEM eye-tracking system's near-infrared emitters had a negligible impact on the prototype VTET sensor system.

Figure 12:
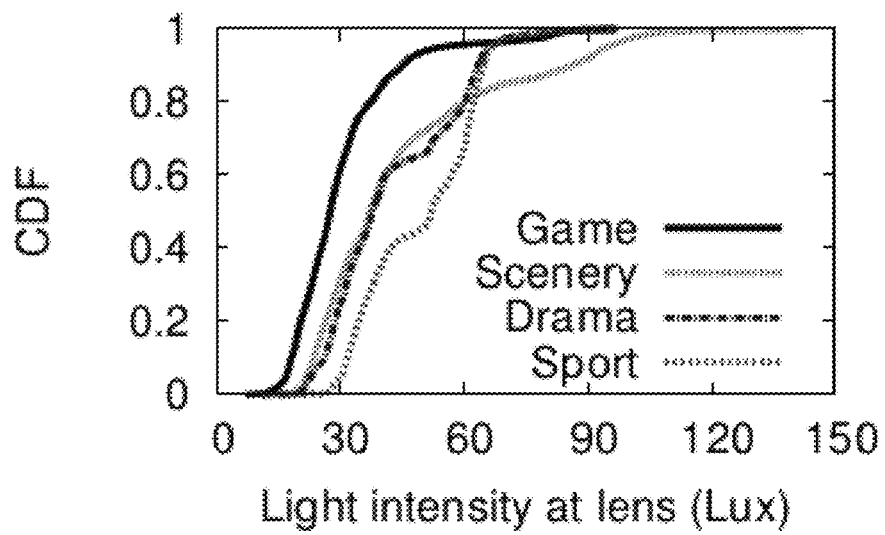
FIG. 12 is a graph of light intensity at a lens of a VR headset under differing VR content types.

In the experiments, each participant wore the headset and watched various VR content. The resulting light intensity at VR lenses was measured as 34 lux on average, with the $5^{th}$ percentile at 20 lux and $95^{th}$ percentile at 75 lux (FIG. 12). The experiment started with two quick calibrations: a 2-min calibration described in Section 2.4.1.1, above to compute W in Eq. (2), and a 1-min game to calibrate parameters in Eq. (3). After calibration, the participant watched 30-min VR content, including drama, sport, scenery, and games. The VR content was randomly selected from a pool for each participant.

To evaluate the prototype VTET sensor system's gaze-tracking performance, four metrics were examined: 1) accuracy: the 3D angular difference between 3D gaze vectors inferred by the prototype VTET sensor system and the OEM eye-tracking system; 2) precision: a measure of stability and reliability of gaze inferences, defined as the variance of the temporally-successive point of gazes; 3) latency: the duration that an online gaze inference takes; and 4) power consumption: the overall power consumption of the prototype VTET sensor system.

2.6.1 Gaze Tracking Accuracy

To examine gaze tracking accuracy, two scenarios were considered: 1) within-user accuracy, where the same participant's data is used to train and test the inference model (25% for training and 75% for testing); 2) cross-user accuracy, where the model is trained using half of participants' data and testing uses the other participants' data. Specifically, the participants were divided into two groups based on their skin colors (light and dark). The inference model was trained and tested separately for each group of participants. Note that within-user accuracy only serves as a reference to examine the prototype VTET sensor system performance if the same user's training data was available). The prototype VTET sensor system did not require training for each new user; rather, it builds an inference model offline using pre-collected training data.

Overall Accuracy. FIG. 13A plots the cumulative distribution functions (CDFs) of within-user and across-user accuracy, over 418,906 gaze inference instances. The mean error is 6.3 and 10.1 with $95^{th}$ percentile at 13.4 and 19.2, for within- and cross-user accuracy, respectively. The spatial pattern of tracking accuracy was examined and the error distribution plotted in FIGS. 13B and 13C. It was observed that tracking error in the center region is smaller (within 5°), while higher tracking errors commonly occur at the boundary of the eye's field of view (FoV). This can be attributed to two factors. First, 40% of the training data contained samples with gazes in the center region. With fewer training samples in border regions, gaze inferences in those regions are less accurate. Further enrichment of the training set can improve the performance. Second, a recent study reports larger tracking errors in screen corners using two commercial IR-based eye trackers. Since the OEM eye-tracking system used a similar methodology (IR-based), it can suffer from similar problems, causing larger deviation between the OEM eye-tracking system's and the prototype VTET sensor system's inferences.

User Diversity. Focusing on cross-user accuracy, we examine the impact of user diversity on gaze inference accuracy. FIGS. 14A and 14B plot the mean accuracy for participants with different skin and eye colors. Error bars covering 90% confidence intervals are also included. It was observed that the average accuracy was similar among different skin colors, as well as eye colors (blue and black). The accuracy of the green-eye participants was lower because only four participants have green eyes. However, the within-user accuracy for these participant is 7.4 on average, indicating that the performance can be greatly improved if there are other participants with green eyes in the training set. It was concluded that it is necessary to have representative eye colors in the training set for robust inference.

VR Content. Next, the impact of VR screen content on the prototype VTET sensor system's gaze-tracking accuracy was examined. The VR screen content was partitioned into four types: drama (quick scene changes), sports (stable background with moving foreground objects), scenery (small, gradual scene change), and games (drastic scene changes). FIG. 15 plots the cross-user accuracy under each content type. It was observed that the accuracy under games was slightly lower. The reason is twofold. First, it was observed that to highlight target objects, game content is generally darker than other content types (FIG. 12). The lower screen light intensity leads to smaller changes in reflected light at photodiodes and thus introduces higher errors in gaze inference. Second, users often rapidly move their gaze directions during games. Since it takes 3.6 ms to collect both reflected light and screen light intensity from all photodiodes, the gaze movement within the data collection data can affect the tracking performance. Due to hardware limitation, the I2C interface's baud rate was limited by its full-speed mode (400 Kbps). The data collection duration can be shortened by using the faster modes such as the fast mode (1 Mbps) or even high-speed mode (3 Mbps).

Accuracy in Estimating Reflected Light. In addition, the accuracy of the linear model in Section 2.4.1.1 was examined in predicting reflected screen light under a center pupil, as it is the basis of the prototype VTET sensor system's gaze inference. For each participant, the weight matrix W was computed using the short (2-min) calibration data. Then, the estimation error was computed as the difference between the estimated and measured reflected light intensity at the back photodiodes. FIG. 16 plots the CDF of reflected light estimation error for all 30 participants. Overall, the estimation is fairly accurate: the mean estimation error is 0.09 lux with 0.38 lux as the $95^{th}$ percentile. Given that the reflected light change is between −1 lux to 2 lux (FIG. 6), the model is sufficient for deriving features related to pupil position.

2.6.2 Gaze Tracking Precision and Latency

Precision. The precision of the prototype VTET sensor system's gaze tracking was measured, which reflects the reproducibility or stability of gaze inferences in spatial domain. It is calculated as the root mean square (RMS) of successive inference results under a fixed gaze. This metric was computed using the gaze inference results during the 5-min calibration, where users stared at screen center. As shown in FIGS. 17A and 17B, the mean precision was 5.2° and 5.9° using the within-user and cross-user model, respectively. Similar to the accuracy distribution, the precision is larger at the boundary of the eye's FoV.

Latency. Table 5, below, shows the latency of the prototype VTET sensor system's main steps. The sensing step includes photodiode sensing duration and the data communication between photodiode and MCU through the I2C board. The feature extraction was mainly on estimating reflected light, with tens of floating-point multiplications. The online gaze inference only included hundreds of floating point additions and tens of floating point multiplications, thanks to the simplicity of the boosted trees regression. Blink detection entailed computing the first-order derivatives of adjacent data points and thus the computation overhead is negligible. Overall, the prototype VTET sensor system generated an inferred gaze vector within 7.8 ms on average, holding the potential to support 128-Hz tracking if photodiodes support higher ADC sampling rates.

TABLE 5

| Steps | Light Sensing | Feature Extraction | Gaze Inference | Blink Detection | Total |
|---|---|---|---|---|---|
| Duration (ms) | 3.6 (±0.1) | 1.5 (±0.15) | 2.6 (±0.15) | 0.1 (±0.01) | 7.8 (±0.4) |

2.6.3 Power Consumption

The prototype VTET sensor system's power consumption was measured using a commercial off-the-shelf power monitor. Table 6, below, lists the power consumed by the main components of the prototype VTET sensor system. Overall the prototype VTET sensor system (sensing and computation) consumed 791 μW on average. The microcontroller unit (MCU) consumed 75% of the total power at 10-Hz tracking rate, where it was active for only 78 ms every second (Table 5). The 32 photodiodes consumed 226 μW because they not only sensed the ambient light intensity, but also digitized the light intensity using the built-in ADCs. The data collection relied on the hardware I2C interface for the MCU to communicate with the photodiodes. Its power consumption can be further lowered down by leveraging dynamic memory allocation (DMA). When the MCU did not infer gaze movement, it entered an ultra-low-power mode (LPM3) with only a few lower-power clocks awake.

TABLE 6

| Components | Mean Power (μW) |
|---|---|
| 32 photodiodes | 226 (±20) |
| Data collection (MCU) | 207 (±15) |

TABLE 6-continued

| Components | Mean Power (μW) |
| --- | --- |
| Feature extraction (MCU) | 120 (±12) |
| Gaze inference (MCU) | 193 (±10) |
| Blink detection (MCU) | 5 (±0.5) |
| Standby (MCU) | 40 (±10) |
| Total | 791 (±67) |

Next, the efficacy of the energy-harvesting unit was evaluated, seeking to examine whether the whole gaze tracking system can be completely powered by the energy harvested from indoor lighting. The harvested power was measured, as was the power loss using our energy-harvesting unit under three levels of indoor lighting. Table 7, below, lists the results and energy conversion ratios. It was observed that once the ambient light is above 400 lux, the prototype VTET sensor system can be powered without additional power. The additional harvested energy in the brighter environments was stored in the super capacitor so that the prototype VTET sensor system could continue tracking gaze movement under temporally dark scenarios caused by user movement and ambient light change. The energy conversion ratio for the energy harvest component remained 86-89% regardless of the ambient light level.

TABLE 7

| Ambient light (Lux) | Harvested power (μW) | Power loss (μW) | Conversion ratio (%) |
| --- | --- | --- | --- |
| 600 | 1091 | 163 | 87 |
| 500 | 924 | 114 | 89 |
| 400 | 788 | 107 | 88 |
| 300 | 589 | 96 | 86 |

To understand the tradeoffs between energy and tracking accuracy, we compared the prototype VTET sensor system to three existing low-power gaze tracking systems: iGaze, iShadow, and CIDER. Since all these systems run in different tracking rates, the energy (in μJ) consumed per gaze inference was examined. For the prototype VTET sensor system, the photodiodes were also down-sampled to examine its performance and energy with fewer photodiodes (e.g., 8, 16). FIG. 18 plots the comparison, where the black line indicates the potential trend of the prototype VTET sensor system in striking the balance between energy and tracking accuracy. It was observed that the prototype VTET sensor system reduced the energy per inference by multiple orders of magnitude, with sacrifices in tracking accuracy. However, with more photodiodes, the prototype VTET sensor system can capture more feature dimensions in boosted trees, which can potentially improve the tracking accuracy. The trend (black line) indicates that with more photodiodes, the prototype VTET sensor system can achieve accuracy comparable to CIDER and iShadow, yet consuming almost half the power. By using photodiodes to capture low-level light signals, the prototype VTET sensor system could adapt the number of photodiodes to specific application needs, making it flexible and efficient. The other systems all relied on cameras capturing hundreds to millions of pixels, where many pixels were often redundant.

2.6.4 Blink Detection

To examine the prototype VTET sensor system's accuracy in blink detection, the precision and recall for all participants was computed, where precision is the percentage of correctly identified blink events among all blink events identified by the prototype VTET sensor system, while recall is the percentage of actual blink events that are identified by the prototype VTET sensor system. Table 8, below, summarizes the results, where 6511 blink instances were collected from 30 participants during the study. The average interval between adjacent blinks is 9.7 seconds across participants, and each blink lasts 0.3 seconds-0.4 seconds. Because of photodiodes' limited ADC sampling rates (10 Hz), the prototype VTET sensor system could only capture up to 4 data points during a blink and it may have missed the data point when a user just closed the eyes. It was also observed that the blink detection was more accurate for users with lighter skin, and the recall for users with black skin was low. This is because the blink detection algorithm assumed an eyelid reflects light well, whereas the reflectivity of black skin is low, leading to more missed blink events. Higher sampling rates can be used to allow the prototype VTET sensor system to capture more data points within a blink instance and extract more detailed temporal features to improve detection accuracy.

2.6.5 Additional Considerations

Head Movement. To examine the impact of head movement on the prototype VTET sensor system, a participant was asked to wear the VR headset and to watch the same VR content for two rounds. In the first round, the participant kept the head still, while in the second round, the participant freely turned their head. As the gaze tracking accuracy was examined in these two rounds, it was observed that the head movement has negligible impact on the average tracking accuracy, where the difference is within 0.8°. It is because unlike other gaze tracking scenarios, in VR, the headset keeps fixed relative positions among the eyes, photodiodes, and the VR display, thanks to the head strap. Thus, the light propagation properties within the headset remains the same regardless of the user head movement, making the system robust against head movement.

User Perception. Since the prototype VTET sensor system adds an annulus PCB on top of each VR lens, it was sought to understand whether the PCB affected user's viewing of VR content. In the experiment, sixteen participants were asked to wear the headset with and without the PCB board for 10 minutes. The participants were then asked to rate their perception of VR content from 1 to 5, where 1 meant the PCB board significantly affects the viewing of VR content, and 5 meant the user cannot feel the PCB board at all while watching the VR content. All users in the study rated the prototype VTET sensor system as 5, demonstrating that the prototype VTET sensor system did not affect user's VR experiences.

Supported Applications. The implications of the prototype VTET sensor system gaze tracking accuracy to end users in practical applications was examined. It was considered using the prototype VTET sensor system to differentiate a few regions in the screen, which can enable simple user input (e.g., selecting/clicking buttons, typing letters or numbers) using only glances. Three settings were tested, where the eye's FoV was split into 2×2, 3×3, and 4×4 grids, respectively. In each setting, the testing data with actual gaze directions (based on the OEM eye-tracking system) within a circular center (30 range) of each grid was selected. Then, it was checked whether the corresponding gaze directions inferred by the prototype VTET sensor system were also within the same grid's circular center. It was observed that the prototype VTET sensor system accurately differentiated different regions, achieving 100%, 99.5%, and 91.7% accuracy under 4, 9, and 16 regions, respectively. This demonstrated that the prototype VTET sensor system could be utilized in a wide range of interaction applications such as dialing phone numbers, navigating VR world, selecting menu items, browsing photo gallery, and controlling the depth of field effect rendering in VR world, among others. A few demo applications were implemented as a proof of concept based on the above scenarios. A user study was conducted with 10 users to gather user feedback on using the prototype VTET sensor system for accomplishing these tasks. Users were asked to rate their satisfaction on both accuracy and latency of the prototype VTET sensor system from 1 to 5, where 5 means high satisfaction. On average, users responded with 4.2 and 4 on accuracy and latency, respectively. This indicates that the prototype VTET sensor system's performance is sufficient for these basic interaction applications.

3. View-Through Sensor with Active Emitters—Example Embodiment

3.1 Methodology and Challenges

In the foregoing example VTET sensor and VTET apparatus in the context of VR, a dual-sided VTET sensor on a VR lens sensed both incoming VR display light and reflected light from the eye. In that example, that design handled incoming light variations by modeling the relationship between sensed incoming light and reflected light. The calibration of the model is possible in VR where a VR screen is the sole light source in a fixed direction and can play judiciously-designed VR content to shorten the calibration for a user. Applying this design for general glasses, however, is generally difficult if not infeasible, given the uncontrolled, diverse nature of ambient light sources. Front sensors cannot provide representative samples of ambient light coming in unknown directions. Also, calibrating the model in diverse ambient light conditions entails heavy overhead.

To address this problem, sensing with NIR emitter was considered, given that ambient light contains much weaker energy in NIR than visible light. An NIR LED was added as a controlled, point light source near the eye. A low-power (it is noted that NIR irradiance power at or below 0.96 mW/cm$^2$ (i.e., 0.42 mW/sr) at eye surface is considered eye-safe), imperceptible NIR emitter beam was then emitted onto the eye in a known direction, while a set of NIR photodiodes circling the eye sensed the NIR emitter reflected by the eyeball after both specular and diffuse reflections. Each photodiode had a limited field-of-view and thus perceived the light reflected only by a small region of the eye. As the pupil moved, it weakened the light reflected in its direction; and as the pupil narrowed or widened during constriction or dilation, it absorbed less or more light, resulting into a global rise or fall of reflected light. Thus, pupil movement and pupillary response resulted in changes in reflected light, providing the basis for tracking the pupil's position and size.

Experimental Validation. To examine the effect of the pupil's light absorption in the glasses context, experiments were conducted with off-the-shelf NIR LED and photodiodes. A PCB hosting 16 photodiodes and 1 NIR LED (it is noted that the LEDs and photodiodes had peak spectrum sensitivity at 940 nm) was fabricated and arranged in a 3.2-cm circle. The LED was placed at the bottom and transmitted at 0.1 mW/sr following the eye-safety standard. The PCB also contained four amplifiers connected to photodiodes. The PCB was then attached to the front of the left lens of a regular pair of eyeglasses, and the board was connected to a microcontroller having a 14-bit ADC that sampled data from photodiodes at 200 KHz.

As illustrated in FIGS. 19A and 19B, the reflected NIR emitter changes upon pupil movement or pupil size variation (e.g., dilation). As the pupil moves from the center to bottom, bottom/top photodiodes perceive declines/increases in NIR emitter intensity because a bottom pupil absorbs more light rays. Pupil dilation, on the other hand, leads to the global decline of reflected light intensity as the pupil absorbs more light.

The impact of ambient light is further examined, since ambient light sources also emit energy in the NIR spectrum. In the experiment, the NIR LED was switched off in the PCB and photodiode data were collected with a user wearing the prototype under nine ambient light settings (Table 6, below). In all settings except direct sunlight, photodiode readings were less than 150, which is close to the noise level given that the maximum ADC value at the microcontroller was 12400 under the 2.5-V reference voltage. This indicated that indoor ambient NIR emitter had a negligible impact on the system. Detailed experiments were conducted that examined the final eye-tracking performance under various ambient light conditions. These experiments are explained in further detail below.

Challenges. To achieve high-performance eye tracking using the above methodology, two main challenges are faced. First, unlike an image sensor or camera, a photodiode or other discrete light-sensing device/region, does not provide any spatial resolution within its field-of-view, rather, only a combined light intensity. Thus, a sub-millimeter pupil movement or size variation can result in negligible differences in reflected light intensities sensed by the photodiodes, which severely limits the system's sensing resolution and accuracy. Furthermore, movement of other structures (e.g., eyelashes, eyelids) in the eye area also affects reflected NIR emitter and interferes with eye tracking. Second, even though photodiodes consume low power, realizing high tracking rates with microwatt-level power consumption is still challenging. Existing methods commonly reduce the sleep duration to achieve high tracking rates. This methodology significantly increases the power consumption to at least a few milliwatts, which is orders of magnitude higher than the amount of power one can harvest from ambient environment (e.g., radio signals, light, thermal or kinetic energy). An alternative method is to interpolate pupil positions based on samples under a low tracking rate. For rapid eye movement during saccades, however, such simple interpolation can cause tracking errors up to 10 mm.

3.2 Multi-Emitter Eye Tracking

A first design element is comprised of designs of both the sensing hardware and the inference algorithm to achieve sub-millimeter tracking accuracy. At the high level, a combination of multiple NIR emitters and an array of photodiodes is proposed. In the present example, NIR emitters are sequentially switched on (with 10-μs switching delay) to emit a short (e.g., 60-μs), directional light beam, while photodiodes sense the spatial pattern of changes in reflected light under each NIR emitter. These sensing data are aggregated, features extracted, and fed to a lightweight regression algorithm to infer the pupil's position and diameter on the fly.

3.2.1 Sensing with Multiple NIR Emitters

In the present example, the VTET sensor's spatial sensing resolution is boosted so that it is capable of differentiating sub-millimeter pupil movements and size variations. A straightforward method is to increase the number of photodiodes while shrinking each photodiode's field-of-view to reduce its spatial ambiguity. The sensing regions of these photodiodes jointly cover the eye surface and can be coupled with one NIR emitter illuminating the eye. With N photodiodes, this method provides N data points at each time instance for pupil inference. Thus, it requires a large number of photodiodes to achieve fine-grained tracking, raising concerns on both the eye tracker's form factor and its power consumption on sensing.

Figures 20A, 20B:
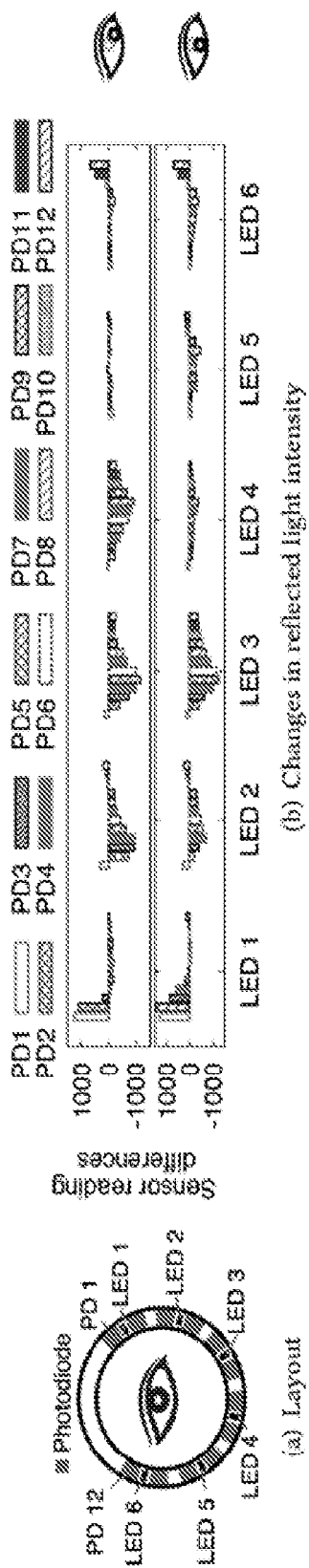

To gather sensing data with a minimal number of hardware elements, M NIR emitters (in the present example, an NIR LED with low radiant power and low duty cycle consumes power similar to that of a photodiode) was coupled with N photodiodes, providing M×N data points with (M+N) hardware components at each time instance. In certain embodiments, M is 2 or more, alternatively 3 or more, alternatively 4 or more, alternatively 5 or more, or alternatively 6 or more. In some such embodiments, M is from 2 to 48, or alternatively from 4 to 24. In certain particular embodiments, M is 6, 8, 10, 12, 14, or 16. In certain embodiments, N is 2 or more, alternatively 3 or more, alternatively 4 or more, alternatively 5 or more, alternatively 6 or more, alternatively 7 or more, alternatively 8 or more, alternatively 9 or more, alternatively 10 or more, alternatively 11 or more, or alternatively 12 or more. In some such embodiments, N is from 2 to 48, alternatively from 4 to 24, or alternatively from 6 to 18. In certain particular embodiments, N is 6, 8, 10, 12, 14, 16, or 18. NIR emitters and photodiodes circled the eye along the boundary of the eyeglasses lens. Their layout was judiciously designed considering the asymmetry of the eye area. Specifically, eyelashes also reflect NIR emitter and interfere with sensing. Thus, photodiodes were not placed at the top of the VTET sensor. An NIR emitter was also not placed near the lateral canthus corner, as it is further from the eyeball and light rays from this direction mostly illuminate the corner skin. FIG. 20A illustrates the layout of NIR emitters and photodiodes in the example NIR VTET sensor. The NIR emitters and photodiodes were slightly tilted so that they better faced the eyeball.

The NIR emitters and photodiodes were regulated as follows. The NIR emitters, in turn, emitted ultra-short, directional light beams from complementary directions onto the eye. In conjunction with each NIR emitter emitting, the photodiodes sensed reflected light at their vantage points, thereby gathering a spatial pattern of changes in reflected light. By separating NIR emitters in the time domain, for a given pupil status, separate snapshots of reflected light patterns under different NIR emitters were obtained. Two pupil statuses may lead to similar spatial light patterns under one emitter while exhibiting different patterns under another emitter. The combination of these patterns/snapshots refined sensing resolution and reduced spatial ambiguity. As an example, FIG. 20B compares spatial patterns of reflected light changes caused by a pupil moving from the center to two positions at the bottom under each light. Given the proximity of the two bottom positions, reflected light patterns were very similar under illumination from some of the NIR LEDs (e.g., LED 2 and 3), while differing more under others (e.g., LED 4). Aggregating these patterns of all emitters better differentiated pupil statuses.

3.2.2. Inferring Pupil Position and Size

With M×N data points (light intensity values) from the photodiodes at time t, another step was to infer the 2D coordinate of the pupil center and pupil diameter at t. In this example, the problem was solved using supervised learning to train offline a personalized model capturing the relationship between the sensing data and pupil status. With the trained model, pupil position and diameter were computed based on the current sensing data. Specifically, the boosted trees regression algorithm was chosen that optimized a sequence of regression trees with weights associated to leaves (decisions). Each new tree helped in correcting errors made by the previously trained tree. A benefit of the boosted trees regression was its low complexity during real-time inference, which involves only comparison and addition operations. The time complexity of the boosted tree regression was less than 10% and 25% of that using feed-forward neural networks and support vector machines (SVMs), respectively. As for tracking accuracy, it was observed that boosted trees actually outperform more complex alternatives, with 3-mm and 0.2-mm smaller mean error than neural networks and SVMs, respectively. It is hypothesized that this was because the experimental scenario did not offer high-dimensional and massive volume of training data for these alternatives to excel. Also, the space complexity of the boosted tree is less than 10% of that for SVMs, making it suitable for a low-power microcontroller. Random forest was another candidate because of its low computation overhead. However, boosted trees can achieve exceptionally higher accuracy than random forest when dimensionality is low (e.g., <4000) and is calibrated, typically making the boosted tree regression a better fit.

Offline Training. A separate boosted trees model for the pupil's coordinate was trained in x and y axis, and the pupil diameter z, respectively. To train the models for a user, 5-minute data was collected where the user was instructed to stare at a ball on a computer screen and follow its moving trajectory. The user wore the eye tracker that collected light-sensing data, as well as a wearable NIR camera that captured eye images. Camera images were later manually labeled to obtain the ground truth of the pupil's 2D positions and leverage software available from Pupil Labs, Berlin, Germany, to acquire the ground truth of pupil diameter.

With M×N data points from light sensing at time t, a feature vector $\mathbb{F}_t$ was extracted with (M×N+M) dimensions, which contained the spatial variations of reflected light across photodiodes under influence of each NIR emitter, as well as the mean reflected light intensity under influence of each emitter. Specifically, let $s_{i,j,t}$ denote the reflected light intensity perceived by photodiode i under NIR emitter j at time t. The mean reflected light intensity was then computed across all photodiodes under light j as $\bar{s}_{j,t}$. $\mathbb{F}_t$ is composed as:

$$\mathbb{F}_t = \{(s_{i,j,t} - \bar{s}_{j,t}), \bar{s}_{j,t} | 1 \leq i \leq N, 1 \leq j \leq M\} \quad (4)$$

The feature vectors $\mathbb{F}_t$ and the pupil's coordinate or diameter were used to train a tree ensemble of K trees with maximum depth h. Five-fold cross-validation was leveraged to fine-tune K and h and set K, h to 50 and 5 respectively, as they achieved the best tradeoff between computation complexity and accuracy.

Online Inference. As light sensing data arrive on the fly, the feature vector is computed as Eq. (4) and fed the feature vector to the trained tree ensembles to compute the pupil's coordinate in each axis and the pupil size separately. Similar to the random forest, each tree will have a prediction score, and the pupil's coordinate is the summation of the K scores.

To improve the energy efficiency of running online inference on an MCU, most floating-point operations were eliminated during online inference. Regression with boosted trees has a large number of floating-point comparisons and additions. Since all features were integers, all comparisons were converted to integers when deploying the regression model to the MCU. For additions, floating-point numbers were approximated by keeping three digits after the decimal point. By left shifting 10 bits, these floating-point numbers were first scaled up to 1024 times and then the results were stored as integers. Some multiplication and division operations could be replaced by shift operations when the multipliers and dividers were multiples of two.

3.3. Adaptive Eye Tracking

A second design element further optimized the energy efficiency of the eye tracking system at a macro level. It examined the sequence of inferred pupil positions to determine the current eye movement stage/type. It then exploited the movement characteristics during the current movement stage to adjust the sensing and computation on pupil inference. It further saved system energy without sacrificing tracking accuracy.

3.3.1 Eye Movement Patterns

Human eyes do not look at scenes with fixed steadiness. Eye movement falls into one of these four types/stages:

Fixation is the stage when gaze focuses on a single location with little pupil movement (below 0.5°). Fixation lasts 150 ms to 500 ms.

Smooth pursuit is the eye movement following a smooth trajectory with relatively constant velocity (30°/s on average), i.e., zero acceleration.

Saccade is rapid eye movement in jumps with varying velocity, which can reach 700°/s with the minimum of 40°/s. A saccade lasts around 200 ms on average.

Blink is the closing and opening of an eyelid to help spread tears and clean the surface of the cornea and conjunctiva. A blink lasts 100 ms to 400 ms and occurs 4 to 26 times per minute, depending on the activity (e.g., reading, conversation).

As examples, FIGS. 21A to 21D plot the pupil's 2D positions and the time series of velocity in various stages. They were samples from the dataset collected by a remote conventional eye tracker.

Figure 21A:
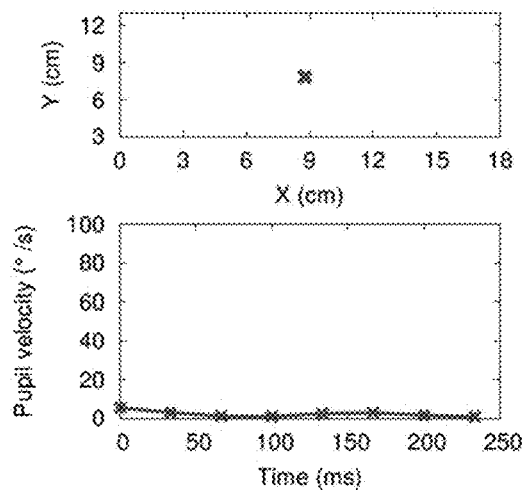
FIG. 21A contains a graph of pupil position (upper) and a graph of velocity (lower) during fixation.
Figure 21B:
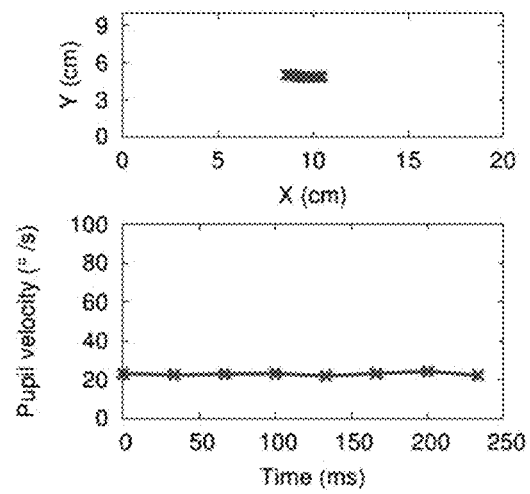
FIG. 21B contains a graph of pupil position (upper) and a graph of velocity (lower) during smooth pursuit.
Figure 21C:
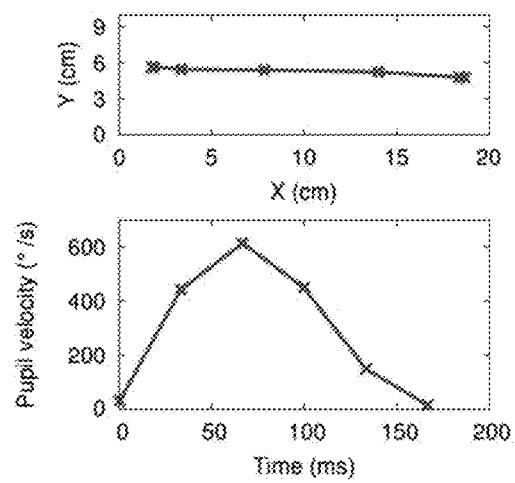
FIG. 21C contains a graph of pupil position (upper) and a graph of velocity (lower) during saccade.
Figure 21D:
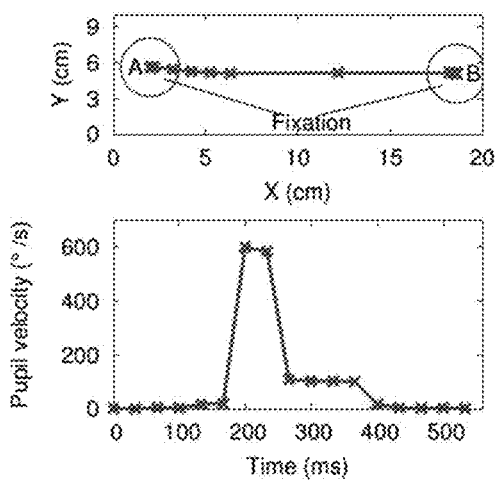
FIG. 21D contains a graph of pupil position (upper) and a graph of velocity (lower) during mixed eye movement.

Continuous eye movement is a sequence of transitions among these stages. As revealed by early research, when scanning a scene or reading, human eyes move in jerks and stop several times, resulting in a series of fixation points with saccadic movements or smooth pursuit in between. The same holds when people look at a picture or watch a movie. FIG. 21D shows a snippet of eye movement sequence as an example, where the movement from location A to B contains two fixation stages, connected by saccadic and smooth pursuit movements.

This interesting eye movement pattern motivates the present inventors to quantify the percentage of each movement stage/type for a variety of common activities. A user study was conducted with 12 participants (10 males and 2 females, 18 to 50+ years old). Two types of scenarios were examined: 1) screen viewing, where each participant sat in front of a laptop screen and performed various tasks including fast reading, slow reading, playing video games, and watching movies; and 2) conversation, where participants are in a meeting and freely look around the environment or stare at other users. Participant's eye movement data was collected at 60 Hz using a remote conventional eye tracker. The dataset contains half-an-hour data for each user in scenario 1) and 15 minutes for scenario 2). The frames of eye blinks were detected and marked by the conventional eye tracker. Remaining movements were then classified into different stages based on their movement velocity and acceleration. Specifically, a prior method was applied where movements with velocity below 5°/s are marked as fixation, those with velocities from 5°/s to 40°/s and acceleration below 1°/s² are smooth pursuit, and those with velocities above 40°/s are saccades. With fixed thresholds, this method can misclassify some movement stages; the results, however, can still indicate the high-level distribution of these stages.

Table 8, below, shows the percentage of each movement stage for each activity, averaged across all participants. The standard deviation is also included in parentheses. The main observation is that regardless of the activity, the majority (80%+) of eye movements are in fixation or smooth pursuit, where fixation occupies a slightly larger portion (43-45%) than smooth pursuit (40-41%). The small standard deviation numbers indicate that the pattern is consistent across participants. One reason that a significant portion of the eye movements is fixations is that it takes time for eyes to fixate on the area of interest, and the brain acquires information during fixations. The observation also aligns with prior studies on eye fixation patterns. In comparison, only 9-15% of eye movements are in saccades, even for tasks (e.g., fast reading) when users rapidly move their eyes all the time. During saccades, the information from the eye is mostly suppressed, and the eye will slow down its velocity to acquire information within areas of the scene. Finally, less than 2% of eye movements are blinks.

TABLE 8

| | Fixation (%) | Smooth pursuit (%) | Saccade (%) | Blink (%) |
|---|---|---|---|---|
| Slow reading | 48.32 (1.57) | 40.54 (1.72) | 9.71 (0.5) | 1.43 (0.11) |
| Fast reading | 45.25 (1.07) | 41.52 (1.27) | 11.34 (0.37) | 1.89 (0.13) |
| Watching movies | 43.84 (2.47) | 41.31 (1.56) | 14.07 (0.59) | 0.78 (0.06) |
| Playing games | 45.6 (4.22) | 41.22 (3.97) | 12.22 (1.3) | 0.97 (0.09) |
| Conversation | 60.85 (5.35) | 32.64 (0.69) | 5.26 (0.33) | 1.25 (0.12) |

Figure 22:
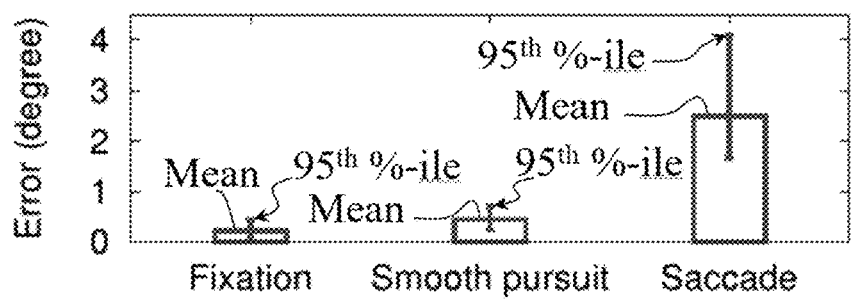
FIG. 22 is a graph of errors of pupil position by linear interpolation.

The predictability of eye movement in each stage (except blink) was further examined. Using the dataset collected in the user study, the data was down-sampled at 30 Hz and linear interpolation was applied to infer pupil positions in the skipped frames. FIG. 22 compares errors of inferred pupil positions across movement stages. For fixation and smooth pursuit, the mean errors were below 0.5° with the 95th percentiles below 10, whereas for saccades, the mean error was 2.5° with 95th percentile above 4°. These results confirm the movement predictability within fixation and smooth pursuit. Saccadic movements in comparison were less predictable.

Overall, the fact that fixation and smooth pursuit dominate the majority of eye movements was encouraging. It indicated that exploiting the movement predictability within these stages can lead to a significant energy saving without sacrificing tracking accuracy.

3.3.2 Adaptation Based on Eye Movement

The characteristics of different eye movement stages are informative to the eye-tracking system's operation. During eye fixation and smooth pursuit, prior pupil positions are highly predictive of the future. Thus, a VTET apparatus of the present disclosure can predict the next sequence of pupil positions fairly accurately using predictive inference, without needing to switch on NIR emitters and photodiodes to gather sensing data and run the full-fledged pupil inference algorithm. During an eye blink, sensing and pupil inference can be switched off as eyelids cover the pupil and sensing data are no longer relevant. Full-fledged sensing and pupil inference generally need to be performed at high rates only for saccadic eye movements.

The challenge of such an adaption is twofold. First, the entry and exit of a moving stage must be timely detected so that sensing and inference are adapted correctly. Quick detection of a movement stage also allows more future inferences within this stage to benefit from predictive inference for more energy savings. Second, since predictive inference relies on prior inference results, it inevitably introduces errors that can accumulate and propagate to future inferences.

These challenges were addressed as follows. First, efficient mechanisms were applied to detect each eye movement stage. The detection threshold was dynamically adjusted based on the current noise level so that the detection was robust against noise-level changes. Second, once detecting the entry of a movement stage, predictive inference was interleaved with the full-fledged sensing and pupil inference. The frequency of running the latter at multiple levels was strategically adjusted. It helped periodically clear the accumulated error from predictive inference while ensuring quick detection of the transition to the next stage. Below, the system flow of the example NIR VTET apparatus is overviewed, followed by the detection and adaptation strategy adopted for each eye movement stage.

Figure 23:
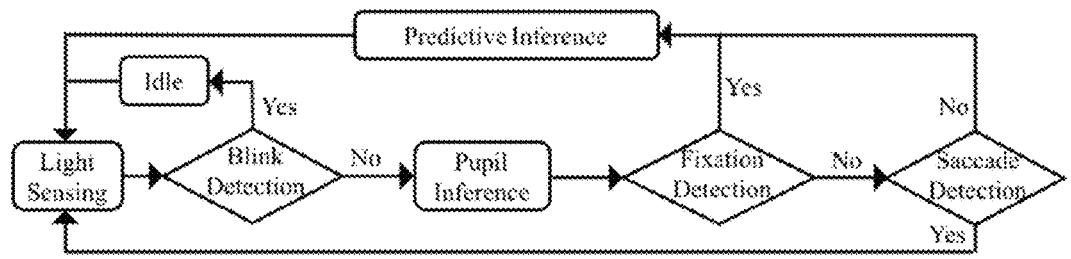
FIG. 23 is a flow diagram illustrating an example system flow of adaptive eye tracking using a VTET apparatus of the present disclosure.

System Flow. As shown in FIG. 23, the example VTET apparatus sampled reflected light intensity values from photodiodes. Based on the sampled data, it first detected whether a blink occurred. If so, the system was switched off for the blink duration. Otherwise, it ran the full-fledged inference algorithm to infer pupil position. Based on pupil position trajectory, velocity, and acceleration, the system detected the eye movement stage and adjusted the rate of sensing and inference accordingly, with predictive inference to provide inferences for skipped frames. Full-fledged sensing and inference were performed at output frame rate only for saccadic movements. Algorithm 1, below, lists the details used in this example. It is noted that in this example the sensing rate was divided by two or four, because such divisions can be implemented as bit shifts, which run faster and consume less power.

---

Algorithm 1: Adapting the rate of sensing and inference.

input: 1) velocities in 40-ms window: $V^x$, $V^y$; 2) acceleration: $a_t$; 3) fixation thresholds: $v_f^x$, $v_f^y$; 4) threshold factors for CFAR: $\alpha_{saccade}$, $\alpha_{blink}$; 5) reference samples and test samples: $R_{saccade}$, $R_{blink}$; 6) the number of LEDs and photodiodes: M, N; 7) output frame rate r output: Eye movement state st, the rate of full-fledged inference r'

```
blink_counter = 0;
for i ← 1 to M do
  | for j ← 1 to N do
  |   | if s_t^{ij} − min(R_blink^{ij}) >
  |   |   α_blink · (median(R_blink^{ij}) − min(R_blink^{ij})) then
  |   |   | blink_counter + +;
  |   | end
  | end
end
if blink_counter > M × N/2 then
  | st = blink;
  | r' = 0; switch off the system for 200 ms;
end
else if V^x < v_f^x & V^y < v_f^y then
  | st = fixation;
  | r' = r/4;
  | T_f = duration( );// fixation duration (ms)
  | if T_f > 200 then
  |   | r' = r/2;
  | end
end
else if a_t > α_saccade · median(R_saccade) then
  | st = saccade; r' = r;
end
else
  | st = smooth pursuit; r' = r/2;
end
```

---

Figure 24:
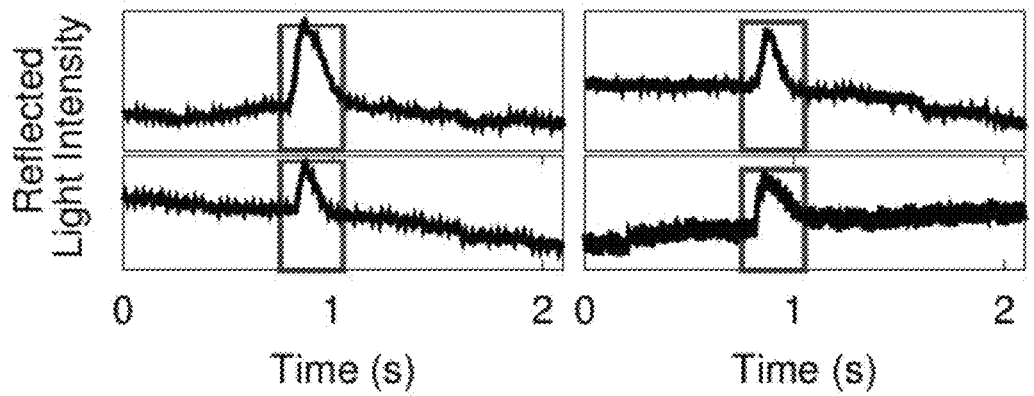
FIG. 24 contains graphs of reflected light intensity changes when a user blinks an eye, with each box representing a blinking instance.

Blink Detection and Adaptation. The spatial correlation of reflected light changes across photodiodes to detect blinks. Unlike pupil movement that weakens reflected light in some directions while strengthening it in others, a blink causes uniform changes in the reflected light across most photodiodes. Because eyelids reflect light when the eyelid covers the pupil, it results in stronger reflected light perceived by photodiodes; when eyelid opens, the pupil continues absorbing light and causes a significant drop in reflected light intensity for most photodiodes. As a result, the eyelid during a blink creates a pulse in the time series of reflected light intensity perceived by most photodiodes. FIG. 24 illustrates an example for four photodiodes when an NIR emitter is on, where each line represents the time series of perceived light intensity at a photodiode.

Based on this phenomenon, blink detection reduces to detecting a dramatic change in reflected light across most photodiodes. A simple method is to compare photodiode signals to a fixed threshold and examine if most photodiodes perceive signal jumps. To set a proper threshold, however, can be difficult, as it is subject to the current noise level that can vary both spatially and temporally. This problem was addressed in the present example by applying constant false alarm rate detection (CFAR) to estimate an adaptive threshold on the fly. CFAR is widely used in the radar systems to detect dramatic signal changes in the noisy background and has been applied in the eye tracking context. In a nutshell, CFAR estimates current noise level by examining m reference samples around the current test sample (i.e., current sensing data). It excludes n samples (i.e., guard samples) adjacent to the test sample to avoid corrupting the noise estimate with the test sample. By adapting the threshold, CFAR maintains a constant probability of false alarm.

CFAR was slightly adjusted in the present example, as traditional CFAR considers reference samples with the test sample in the center, whereas in this example test sample were the latest sensing data. Thus, m samples were considered before the test sample as the reference samples. Let $s_t^{ij}$ denote the test sample, i.e., the light intensity value at photodiode i when NIR emitter j is on. The set $R_{blink}^{ij}$ of reference samples for this pair of photodiode and light contains $s_{t-n-m}^{ij}$, $s_{t-n-m+1}^{ij}$, . . . , $s_{t-n-1}^{ij}$. then a blink was detected if the following condition holds for at least half of the light-photodiode pairs:

$$(s_t^{ij} - \min(R_{blink}^{ij})) > \alpha \cdot (\text{median}(R_{blink}^{ij}) - \min(R_{blink}^{ij})) \quad (5)$$

where $\alpha$ is the threshold factor. It is calculated as:

$$\alpha = f(1-P_{fa})/f(\tfrac{1}{2}) \quad (6)$$

where $f$ is the error function and $P_{fa}$ is the false alarm rate. In this implementation, we set m, n, and $P_{fa}$ as 20, 10, and $1e^{-2}$ respectively, and $f$ was a Gaussian error function as it was observed that sensor errors followed a zero-mean normal distribution.

Once a blink was detected, the example VTET apparatus switched to the idle mode for 200 ms without performing any sensing or inference, given that a blink lasts around 250 ms on average. After 200 ms, the example VTET apparatus continued sensing and full-fledged inferencing at its output frame rate r. Based on the inferred pupil positions, the detection of different pupil movement stages and corresponding adaptation were introduced.

Fixation Detection & Adaptation. Fixation using a threshold-based method was detected. Since the mean fixation duration is around 250 ms, pupil positions were examined within a 40-ms sliding window (or 6 frames@120 Hz) to determine the entry of fixation. Let $(x_t, y_t)$ denote the pupil's position at time t, and T be the time interval between two adjacent inferences. Pupil's movement velocity WAS estimated in x- and y-axis at time t as:

$$u_t^x = \frac{x_t - x_{t-2}}{2T}, \quad (7)$$
$$v_t^y = \frac{y_t - y_{t-2}}{2T}$$

If both velocities were below threshold $\upsilon_f^x$ and $\upsilon_f^y$ respectively, then the fixation test at time t is passed. If such test is passed for all positions in the sliding window (i.e., from time t to (t-5)@120 Hz), then the system marked the current stage as fixation. $\upsilon_f^x$ is set as 5°/s and $\upsilon_f^y$ as 3°/s, based on prior studies and experiments. It is noted that adaptive thresholds brought negligible gains for fixation detection because velocity was near zero. The example VTET apparatus kept conducting this fixation test for every subsequent pupil position. It exited the fixation stage whenever the test failed, ensuring that the VTET apparatus can timely detect the exit of fixation.

Upon the detection of the entry to fixation, the system lowered the frequency of conducting sensing and full-fledged inference to r/4 for the next 200 ms, where r is the output frame rate of inference results. The skipped frames in between were provided by predictive inference to maintain the output frame rate as r. Predictive inference for fixation is simply the previous pupil position given that the pupil rarely moves. Within the 200 ms, if the fixation test failed at any time point, the example VTET apparatus immediately treated it as the exit of fixation and returned the frequency of sensing and inference to r. If the fixation stage remained after 200 ms, statistically the pupil was likely to exit fixation anytime soon. To ensure timely detection of exit, the example VTET apparatus increased the frequency of sensing and full-fledged inference to r/2.

Upon the detection of the exit of fixation, the example VTET apparatus further examined whether the current movement is saccadic using the following method.

Saccade Detection & Adaptation. Saccade detection was based on the sudden, significant jump in acceleration. Acceleration was used rather than velocity because the velocity ranges of smooth pursuits and saccades overlap. Instead of setting a fixed threshold for the acceleration, the CFAR method was applied to estimate the proper threshold on the fly and detected the entry of a saccade. In comparison to a fixed threshold, the adaptive threshold was more robust against noises that can change both spatially and temporally. If the threshold was too high, many saccades will be treated as smooth pursuits, which degraded tracking accuracy. If the threshold was too low, the example VTET apparatus would miss many smooth pursuits and thus opportunities for energy saving. CFAR adapted the threshold to maintain a constant probability of false alarm, which balanced the tracking performance and energy efficiency.

Specifically, let $a_t$ denote current acceleration (i.e., test sample) at one axis. The adaptive acceleration threshold for each axis is derived by estimating the noise level around $a_t$. Similarly to blink detection, the set $R_{saccade}$ of m reference samples contained $a_{t-n-m}, a_{t-n-m+1}, \ldots, a_{t-n-1}$. Then the entry of a saccade is detected if the following condition holds in both x- and y-axis:

$$a_t > \alpha \cdot \text{median}(R_{saccade}) \quad (8)$$

where $\alpha$ is the threshold factor calculated as Eq. (6). m, n, and $P_{fa}$ were set as 20, 10, and $1e^{-3}$ respectively in the implementation. To minimize the computation overhead, $a_t$ was rectified by an absolute value operator. With this simple design, online saccade detection mainly involved computing the median of m numbers in $R_{saccade}$. A red-black tree and a circular buffer were leveraged to minimize the overhead.

Once detecting a saccade, the example VTET apparatus maintained the frequency of sensing and full-fledged inference as r. Otherwise, the example VTET apparatus marked the current stage as a smooth pursuit, set the full-fledged inference rate as r/2, and applied linear interpolation as the predictive inference to infer skipped frames.

3.4 Prototype Implementation

Figures 25A, 25B, 25C:
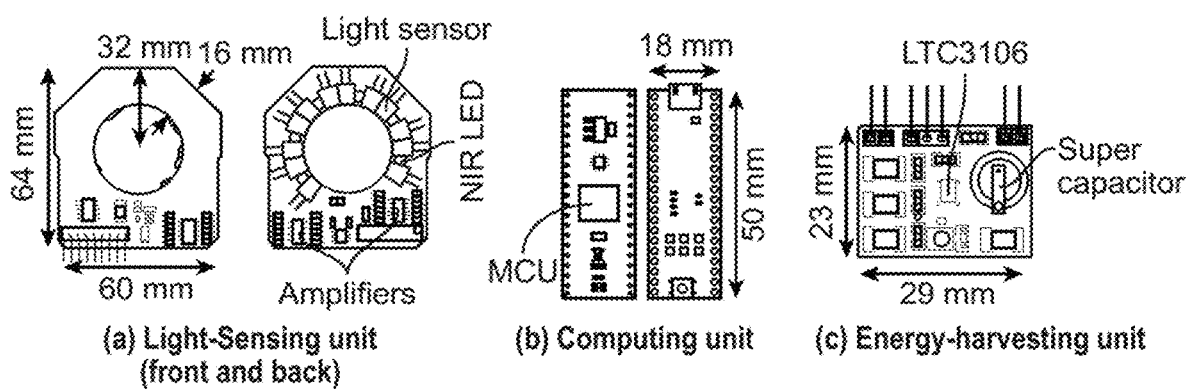
FIG. 25A contains photographs of the front and back sides of an NIR VTET sensor of an example prototype VTET apparatus of the present disclosure.
FIG. 25B contains photographs of the front and back sides of a computing unit of the prototype VTET apparatus of FIG. 25A.
FIG. 25C is a photograph of an energy harvesting unit of the prototype VTET apparatus of FIG. 25A.

A compact and lightweight (<25 g) example prototype VTET apparatus has been built using off-the-shelf hardware components. The prototype comprises three components, namely an NIR VTET sensor, a computing unit, and an energy harvesting unit (FIGS. 25A to 25C, respectively).

VTET Sensor. A thin (0.8-mm) PCB (<10 g) was designed and fabricated that hosted 6 NIR LEDs and 12 photodiodes, both with peak spectrum sensitivity at 940 nm. LEDs and photodiodes were slightly tilted so that each LED's 3 dB-beam covered 70% of eye surface and each photodiode perceived 50% of eye surface within its 3 dB field-of-view. The type of LEDs was chosen for two reasons. First, its spectral sensitivity range was narrow (80 nm) and far from the visible light spectrum, which filters out ambient visible light interference. Second, with ±60° 3 dB field-of-view, it could perceive more reflected light rays from the eye even at a short distance (<2 cm). The type of photodiode was chosen because it leveraged the manufacturer's new surface emitting technology, which saves up to five times energy compared with standard emitter technology. A current flow control component was added to trigger LEDs sequentially and limit the radiant intensity to 0.1 mW/sr, which is much lower than the infrared irradiance standard for eye safety. Three 4-channel, low-power amplifiers were added to amplify signals from photodiodes. Each amplifier contained a built-in low-power supply (4 μA per amplifier at maximum), low-offset voltage (1.5 mV), and low-bias current (3 nA), which help further reduce the power consumption of the sensing unit and improve the signal-to-noise (SNR) ratio.

Computing Unit. A microcontroller board was used to digitize analog signals from amplifiers, extract features, detect eye movement stages, and infer pupil positions. The microcontroller unit was an ultra-low-power MCU with 80 μA/MHz in the active mode. It embedded a low-power ADC with 400 μA at 1 Msps. During signal digitization, the embedded direct memory access (DMA) was leveraged to maximize ADC rate and reduce energy consumption. Inference results were stored in the MCU. They could also be transmitted to other devices through a UART port or battery-free wireless transmissions.

Energy Harvester. The system harvested energy from ambient light to power all its operations. Light was chosen because of its higher energy density compared to other energy sources. The harvester leveraged two 11.4×3.7 cm thin-film solar cells, which provided high short-circuit current with improved harvesting efficiency. Also, as thin (0.2 mm), bendable films, they were lightweight and flexible to attach to the side arms of eyeglasses.

The harvested energy could vary due to user movement (e.g., walking, head movement) and ambient light fluctuations. It could even occasionally fall below the example prototype VTET apparatus's required power. To deal with energy fluctuations, a buck-boost DC/DC converter and a super-capacitor (0.22 F) were used. The buck-boost DC/DC converter stabilized the output voltage (at 3.3V), while the super-capacitor stored extra energy when the harvested energy exceeded the currently consumed power. The stored energy could supply the system when the instantaneously harvested power was insufficient.

3.5 Prototype Experiments

Twenty-two participants (8 females) were recruited to evaluate the prototype. Two of them wear contact lens. Table 9, below, summarizes participant information.

TABLE 9

|  | Eye Color | | | Skin Color | | |
| --- | --- | --- | --- | --- | --- | --- |
|  | Black | Blue | Green | White | Yellow | Black |
| # of Users | 16 | 5 | 1 | 6 | 11 | 5 |

Experimental Setup. The prototype was augmented with a small infrared camera to acquire the ground truth. Specifically, the camera was installed in front of the eye (2.5 cm away) using a 3D-printed holder glued to the prototype. The camera was connected to a computer board and set the frame rate to its maximum (120 FPS) and image resolution to 320×240. To synchronize camera images and light sensing data, three NIR LEDs (940 nm) were added next to the camera and these LEDs were programmed to emit an 8-ms light pulse at the beginning of each experiment. It led to a sudden brightening of the image and a rise in photodiode readings. This feature was exploited to identify the first camera image frame and the first sample of light sensing data. A separate experiment was conducted with 12 out of 22 participants to evaluate the pupil diameter inference. In the experiment, the camera ran at 60 FPS with image resolution of 640×480.

With this augmented prototype, training and testing data was collected from each participant. The training phase lasted 5 minutes, where each participant wore the prototype, sat in front of a computer screen, and stared at a moving red ball on the screen. The red ball was programmed to move along a smooth zigzag path scanning the screen. This maximized the number of pupil positions in the training data during this short data-collection period. Overall roughly 35,000 frames were collected on average per participant (769,710 frames for all participants). To obtain the ground truth, the pupil center and blink status was manually labeled in each image frame. The application programming interface (API) of the Pupil Lab's software, mentioned above, was leveraged to extract the pupil shape (e.g., oval) and derive the pupil diameter as the length of the oval's long axis. To improve labeling accuracy, blurred or overexposed images were skipped. Light sensing data and the ground truth were used to train a personalized inference model for each participant. The offline training was done on a desktop, and the computation took less than 10 seconds.

In the testing phase, each participant performed the five activities in Table 8, above, while wearing the prototype running the trained personalized model. The system computed and stored inferred pupil positions and diameters on the fly. Each activity lasted one minute, during which participants could freely move their heads and choose the content or scene to view. In total, 721,846 frames were collected for testing. Similarly, the ground truth was obtained through manual labeling, which were then compared to the online inference results to evaluate the prototype's tracking performance.

Error Metric. The error metric used was the distance deviation between inferred and ground-truth pupil center or diameter. Angular error was not chosen as the metric because deriving the gaze vector from an image accurately (e.g., <0.5° error) required either multiple cameras to extract optical axis of the eye, or high-resolution images (e.g., 640×480) to locate the glint position on the image. The hardware setup had only one wearable camera with image resolution of 320×240 at 120 FPS (the output rate of this inference). Thus, estimated gaze vectors were less accurate than labeled pupil centers and diameters.

3.5.1 Accuracy and Precision

Overall Accuracy. Two variants of the method were considered for comparison:

1) running sensing and inference at 120 Hz without the adaption in Section 3.3, above, and 2) applying adaptation with fixed thresholds for detecting eye movement stages. The first variant served as an upper bound to examine possible sacrifice in accuracy by adding predictive inference. The second variant examined the contribution of adaptive thresholds.

Figures 26A, 26B:
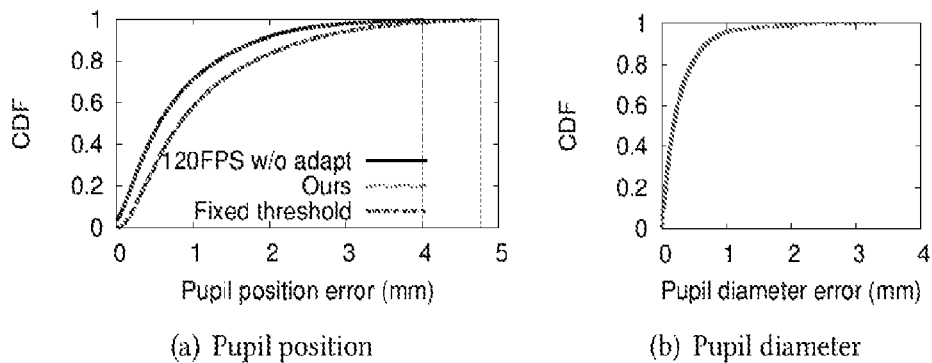
FIG. 26A is a graph illustrating accuracy of tracking pupil position for the prototype VTET apparatus of FIG. 25A.
FIG. 26B is a graph illustrating accuracy of tracking pupil diameter for the prototype VTET apparatus of FIG. 25A.

FIG. 26A plots the CDFs of tracking errors of pupil positions for all participants. Overall, the example prototype VTET apparatus achieved 0.8-mm mean tracking accuracy with 2.3 mm at the 95th-percentile and 4 mm as the maximum. Comparing it to the variant without any adaptation, the negligible difference (<0.01 mm) was observed. This indicates that the adaption mechanism properly skipped sensing and inference during predictive eye movements and thus entailed minimal sacrifice on tracking accuracy. Comparing to the variant with fixed thresholds, the method was most effective in improving the tail performance, with a reduction of 0.77 mm at the maximal error and 0.4 mm at the 95th percentile. The reduction was moderate because adaptive thresholds were only applied for detecting blinks, saccades, and thus smooth pursuit. The reduction in tracking error for these types of eye movements, however, was valuable, since measures of these movements were effective clinical metrics. The results show adaptive thresholds were effective in identifying eye movement transitions.

FIG. 26B plots the CDF of tracking errors in pupil diameter. The mean error was 0.3 mm with 0.9 mm at the 95th-percentile and 3.4 mm as the maximum. Slightly larger errors during saccades were observed. The reason was that reflected light was affected by both pupil size variation and pupil movement. During saccades, the impact of pupil movement on reflected light was more significant than that of pupil size variation, which degraded the accuracy of size inference. Currently, a separate model was trained for inferring pupil position and size. A joint model can also be considered to combine pupil position and size in the training phase.

Figures 26C, 26D:
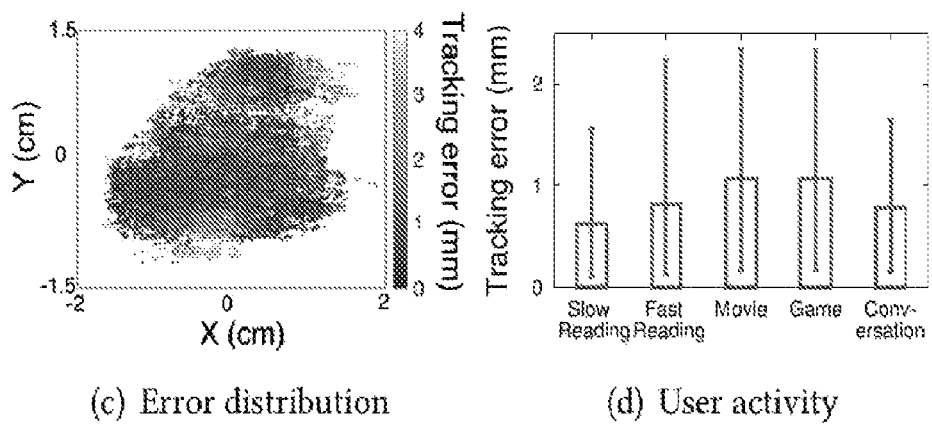
FIG. 26C is a graph illustrating the spatial distribution of pupil position errors for the prototype VTET apparatus of FIG. 25A.
FIG. 26D is a graph showing the error across activities for the prototype VTET apparatus of FIG. 25A.

Error Spatial Distribution. The distribution of tracking errors in the spatial domain was analyzed and the average tracking error was plotted for each pupil center position in FIG. 26C. For 80%+ positions, the mean tracking error was observed as being less than 1 mm. The larger errors mostly occur when the pupil moved to the vision boundary. In these scenarios, the pupil was partially occluded, which degraded the accuracy.

User Activity. The eye movement patterns can vary across activities, which in turn affect the manner the system adapts its sensing and inference. To gain a better understanding of the impact of user activity, tracking accuracy was analyzed across different activities. For each activity, the results across participants were aggregated and the average tracking error in FIG. 26D was plotted. Error bars were also included covering 90% confidence intervals. Tracking errors during gaming and watching movies were observed as being slightly higher than others. Further analysis showed that the percentages of saccadic eye movements were much higher during those activities (13% and 12%, respectively). As a result, the mean velocity and acceleration of pupil movement were at least three times higher than that of other activities. With 120-Hz tracking rate, it took at least 8.3 ms for the example prototype VTET apparatus to detect transitions of pupil movement stages, which introduced errors in capturing rapid transitions.

Figure 27:
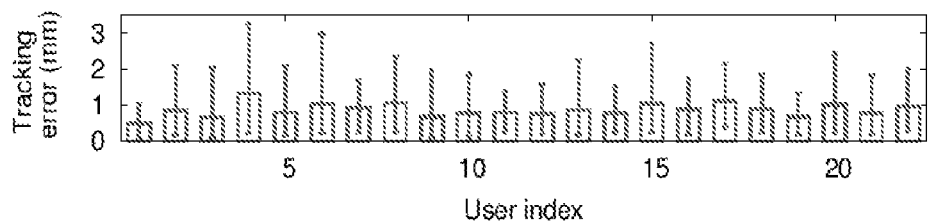
FIG. 27 is a graph of pupil position error for each participant for the prototype VTET apparatus of FIG. 25A.

User Diversity. It was further analyzed how tracking accuracy was affected by individual differences in skin/eye color and eye movement pattern. Each participant's inference results were aggregated and in FIG. 27 plotted the average and 90% confidence interval as the error bar. The differences in mean pupil position errors were observed as being within 0.8 mm across participants. In comparison, the results of user 1 were the most accurate (0.5-mm mean, 1 mm at the 95th per-centile), while that of user 4 had the largest error (1.3-mm mean, 3.2 mm at the 95th percentile). Analysis of user 4's data revealed that this participant had the highest mean pupil acceleration and velocity during the experiment, leading to higher tracking errors.

Precision. The system's precision, a measure of stability and reliability of pupil position inferences under a fixed gaze, was examined. It reflected the ability of the eye tracker to reliably reproduce a measurement and has been widely adopted by existing eye-tracking research. Precision was computed by the root mean square (RMS) from the successive data points when the user looked at a fixed point. The mean precision for the system was 0.4 mm and the large errors mostly occur around the vision boundary.

3.5.2 Detection of Eye Movement Types

Next, the accuracy in detecting various eye movement stages (blinks, fixation, and saccade) was evaluated. In Table 10, below, the precision, recall, and F1 score based on the data of all participants was listed. Precision was the ratio of correctly detected blink instances within all detected blink instances. Recall was the ratio of detected blink instances within all actual blink instances. The F1 score was the harmonic average of precision and recall. Overall, all movement stages were detected with 90%+ accuracy. For blink detection, some false detections were due to the sudden movement of the glasses frame. It caused drastic signal changes at most photodiodes and could trigger the system to treat it as a blink mistakenly. For fixation detection, its errors were related to tracking errors of pupil position, since a fixation was detected based on the pupil movement velocity (3°/s or 1.5 mm/s). Large errors in pupil position (e.g., >1.5 mm, 15% of the tracking results in FIG. 26A) could cause wrong fixation detection. Additionally, for all tested activities (Table 8, above) with all participants, blinks, fixations, and saccades were observed to occupy 1.19%, 49.37%, and 8.16% of the total frames, leaving 41.27% for smooth pursuits. The result aligned with prior observations in Table 8, above. It confirmed that regardless of user activities, eye movement was predictable in the majority of cases because of its jerky nature.

TABLE 10

|  | # of Frames | Precision | Recall | F1 |
|---|---|---|---|---|
| Blink | 8,589 (1.19%) | 0.933 | 0.947 | 0.94 |
| Fixation | 356,375 (4937%) | 0.921 | 0.916 | 0.92 |
| Saccade | 58,902 (8.16%) | 0.918 | 0.935 | 0.93 |

3.5.3 Latency

Tracking latency was next examined, which was defined as the duration to produce a pupil inference. Table 11, below, lists the latency of each key step to produce an inference. Overall, pupil inference and the movement detection ran fairly fast, and the light sensing step dominated the latency. The light sensing step included sequentially switching on each NIR LED while photodiodes sensed reflected light under each LED. The latency came from three components: 1) 40 µs for the pinout setups on the microcontroller; 2) 360 µs for acquiring a set of M×N (=72) data points, given that the microcontroller sampled at 200 Ksps; and 3) 10-µs delay before switching to another LED, which helped photodiodes and amplifiers better respond to NIR emitter intensity change. The inference computation took 160 µs to infer a pupil position. For higher efficiency, inference subtasks were executed during each 10-µs switching delay. It resulted in an overall latency of 560 µs for one inference, potentially supporting tracking above 1.7 KHz.

TABLE 11

| Steps | Light Sensing | Movement Detection | Pupil Inference | Total |
|---|---|---|---|---|
| Latency (µs) | 450 (±20) | <1 | 160 (±5) | 560 (±25) |

3.5.4 Energy Consumption

The power consumption of the prototype was also examined. Table 12, below, lists the energy consumed by the key components to produce an inference result. Pupil inference here referred to the full-fledged inference in Section 3.2.1, above. Overall, each inference consumed less than 6 µJ, with signal digitization (2.5 µJ) and the inference algorithm (2.4 µJ) as the main contributors. Light emission and sensing consumed less than 1 µJ (<17% of the total consumption), where the peak power of each NIR LED was less than 0.5 mW. The energy consumption could possibly be further reduced with ultra-low power ADCs. When the system did not perform any sensing or computation (e.g., during a blink), the MCU remained at the ultra-low-power mode and the light-sensing board would be shut down. The power consumption in this mode was less than 40 µW.

TABLE 12

|  | Light-Sensing Unit | | Micro-Controller | | |
|---|---|---|---|---|---|
|  | Photodiodes | IR emitters | ADC | Movement detection | Pupil Inference |
| Energy (µJ) | 0.5 (±0.04) | 0.4 (±0.05) | 2.5 (±0.08) | <0.1 | 2.4 (±0.07) |

The power consumption was further examined with the adaption strategy in Section 3.3, above. Since the actual adaptation depends on user activities, the average power consumption was plotted for each activity in FIG. 28A. The result for the method was also included without any adaption (i.e., running full-fledged sensing and inference at 120 Hz) as a baseline. The error bars cover 90% confidence intervals. Overall, the mean power consumption of the system across all activities was 395 µW, which was 52% of the power consumed by the baseline without any adaption. The energy saving came from the predictive eye movement types (i.e., fixation, smooth pursuit) and blinks. As shown in Table 8, above, and Section 3.5.2, above, these predictive movement types occupied 86% of all frames even in activities with rapid eye movement (e.g., gaming). This was because of the inherent characteristics of the eye movement (moving in jerks). Thus, a large portion of inferences was realized as predictive inferences using the adaptation scheme, leading to significant energy savings. Across activities, the power consumption under games and videos was slightly higher. It was because more saccades occur during these activities and the system skips fewer frames to run the full-fledged sensing and inference.

Next, the system was compared with four existing low-power eye trackers (LiGaze, CIDER, iShadow, and iGaze), by examining their tradeoff between tracking accuracy and power consumption. Since each system ran at a different tracking rate, they were compared by energy consumption per inference. Given that some report only angular errors, these angular errors were converted to distance deviations for a fair comparison. In particular, an emmetropic human adult eye was leveraged where the normal horizontal rotation range of an eye was [−35°, 35°], and the pupil horizontal movement was within [−18 mm, 18 mm]. Thus, 1° angular error maps to 18/35 mm distance deviation. FIG. 28B shows the comparison. The power consumption of the system has been observed to be several orders of magnitudes lower than existing methods without sacrificing much in tracking accuracy. The system's tracking performance was comparable to CIDER, which achieved the best tracking performance using cameras.

3.5.5 Energy Harvesting

The energy-harvesting unit in typical room settings has been evaluated and has shown its capability to power the entire system indoors. Although solar energy harvesting has been studied extensively in the literature, there have been no systematic measurements with setups similar to these (solar cells vertically placed on the glasses side arms) under various user activities. Four ambient light settings were tested with light intensity ranging from 300 lux to 900 lux: 1) a 60 $m^2$ office with four fluorescent lights on the ceiling (2.6-m height). The light intensity at day and night was 700 lux and 500 lux, respectively, at a 70-cm high table; 2) the same office as 1), where three LED floor lamps were added emitting lights from sides; 3) the same office as 1), where only the floor lamps were turned on. The light intensity at day and night was 500 lux and 300 lux, respectively, at a 70-cm high table; 4) a 18 $m^2$ lab space with LED panels on the ceiling. The light intensity at day and night are 900 lux and 800 lux, respectively, at a 70-cm high table. These settings were chosen based on the recommended light levels by the US National Research & Development Center and Illuminating Engineering Society (IES). The illumination for normal office work, library, laboratories was recommended to be above 500 lux. The 300-lux setting was below the standard and was used only to test low-light conditions. In each setting, scenarios were tested when the user was sitting, standing, or walking while wearing the prototype with solar cells on the glasses arms.

FIGS. 29A and 29B plot, respectively, the harvested power in each daytime and nighttime settings. First, both light source positions and user activities affected the amount of energy that can be harvested. Since most indoor lights are on the ceiling, when users stand up or walk, solar cells are closer to light sources and harvest more energy. For floor lamps, some of their emitted light rays are perpendicular to the solar cells on glasses arms, allowing more power to be harvested. Second, across the luminary types, the energy harvester acquires more power under fluorescent lights than LEDs. As a less efficient luminary type, fluorescent lights radiate more heat and contain more infrared light, which can be converted to energy more efficiently by solar cells. Third, the harvested power was above the system's requirement (395 μW) in most settings when ambient light was above 500 lux, except at night when the user was sitting on a chair. Under the low-light condition (e.g., 300 lux), the super-capacitor, which stored surplus energy from other light conditions, could compensate for the power gap. For example, after one-hour normal usage in setting 2 during the daytime, the surplus power in the super-capacitor could support the system for one hour in setting 3 at night.

3.6 Additional Considerations

Eyeglasses Movement. Eyeglasses can slightly move during reading or user movement (e.g., walking). To analyze its impact on performance of the prototype VTET apparatus, a participant was instructed to wear the prototype VTET apparatus and to slightly move the eyeglasses frame from the normal position on the nose by various offsets up to 2 cm, where with 2-cm offset, the eyeglasses frame was on the tip of the participant's nose. FIG. 30A shows the mean tracking error of the pupil position, where error bars cover 90% confidence intervals. The error increase was very small when the offset was within 8 mm. In these cases, the eye center changed up to 2 mm in the camera's view, and the sensing data changed up to 2%, compared with that without any offset. Thus, the regression model could handle these small deviations in features/labels. However, for larger offsets (e.g., 2 cm), the eye center could move up to 15 mm in the camera view and sensing data could change up to 20%, leading to much larger errors. To enhance the prototype VTET apparatus's robustness against glasses movement, more training data can be collected with various glasses offsets.

Ambient Light. The performance of the prototype VTET apparatus was tested under nine ambient light conditions with various types of light sources, light directions, and light intensity levels. Table 13, below, shows the mean and standard deviation of sensor readings (12400 is the maximal reading with 2.5-V reference voltage) when a user wore the prototype VTET apparatus with all NIR LEDs switched off. Thus, these data indicated ambient NIR energy levels in various indoor settings. FIG. 30B shows the tracking error of the pupil position, including 90% confidence intervals, in each light condition. Overall, the prototype VTET apparatus was robust across these conditions, except strong direct sunlight (104 lux), which contained strong NIR energy. NIR energy radiated by indoor light sources or indirect sunlight has a negligible impact on the system. In these settings, the ambient NIR energy maps to sensor readings within 100 to 150, whereas with these NIR LEDs, sensor readings vary between 1500 and 11000 in the dark environment. However, direct sunlight maps to sensor readings up to 2500, which can saturate sensors when these NIR LEDs are on and degrade the tracking performance. To mitigate this problem, the sensor gain can be adapted to avoid saturation.

TABLE 13

| # | Type of Light Source | Light Source Position | Ambient Light Intensity (Lux) | Sensing Data (Mean/Std.) |
|---|---|---|---|---|
| 1 | LED Light | Uniform | 300 | 5/1 |
| 2 | LED Light | Uniform, Front Back, Left, Right | 600 | 7/2 |
| 3 | Fluorescent Light | Uniform | 600 | 30/7 |
| 4 | Incandescent Light | Uniform | 600 | 47/11 |
| 5 | LED Light | Uniform | 800 | 35/9 |
| 6 | Non-direct Sunlight | Window | 1000 | 85/16 |
| 7 | Non-direct Sunlight | Window | 2000 | 141/26 |

TABLE 13-continued

| # | Type of Light Source | Light Source Position | Ambient Light Intensity (Lux) | Sensing Data (Mean/Std.) |
|---|---|---|---|---|
| 8 | Direct Sunlight | Window | 5000 | 934/86 |
| 9 | Direct Sunlight | Window | 10000 | 2526/205 |

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for tracking eye movement of a subject eye of a user, wherein the subject eye has a pupil and an exterior, the apparatus comprising:
   a support structure;
   a view-through sensor secured to the support structure for tracking eye movement via light reflected from the exterior of the eye when the user is wearing the support structure, the view-through sensor having:
   a view-through region that allows the user to see through the view-through sensor substantially unobstructed during use of the apparatus; and
   a peripheral active device region adjacent to the view-through region and at least partially surrounding the view-through region, the peripheral active device region containing a first plurality of light-sensing regions distributed around the view-through region and be operative, separately from one another, to sense intensity of light reflecting off of the exterior of the subject eye and striking the first plurality of light-sensing regions while the user is looking through the view-through region; and
   a processor, and machine-executable instructions that, when executed by the processor, execute a gaze-inference algorithm that determines a location of the pupil of the subject eye as a function of light-intensity readings made from the first plurality of light-sensing regions while the user is looking through the view-through region and based on light passing through the pupil into the subject eye and absorbed within the subject eye.

2. The apparatus according to claim 1, wherein the support structure comprises a lens and the view-through sensor is located adjacent to the lens so that viewing through the view-through region allows the user to see through the lens.

3. The apparatus according to claim 2, wherein the support structure comprises a virtual-reality headset that includes the lens.

4. The apparatus according to claim 2, wherein the support structure comprises an eyeglasses frame supporting the lens.

5. The apparatus according to claim 4, wherein eyeglasses frame is part of augmented reality eyewear.

6. The apparatus according to claim 1, wherein the first plurality of light sensing regions contain a plurality of corresponding respective visible light sensor devices, and the intensity of the light reflecting off of the exterior of the subject eye is intensity of visible light reflecting off of the exterior of the subject eye as perceived by the visible light sensor devices.

7. The apparatus according to claim 6, wherein each of the plurality of visible light sensor devices comprises a photodiode.

8. The apparatus according to claim 1, wherein the machine-executable instructions further comprise machine-executable instructions that, when executed by the processor, execute a gaze-inference algorithm that determines the location and a diameter of the pupil of the subject eye as a function of light-intensity readings from the first plurality of light-sensing regions during use of the apparatus and based on light passing through the subject eye and absorbed within the subject eye.

9. The apparatus according to claim 8, wherein the machine-executable instructions further comprise machine-executable instructions that, when executed by the processor, execute a predictive inferencing algorithm for predicting a future location of the pupil of the subject eye, and adapt the execution of predictive inference based on the type of the current eye movement.

10. The apparatus according to claim 1, wherein each of the first plurality of light sensing regions is responsive to visible light.

11. The apparatus according to claim 1, wherein the view-through sensor uses environmental visible light for eye tracking.

12. The apparatus according to claim 11, wherein the first plurality of light-sensing regions is located on an obverse side of the view-through sensor, the view-through sensor further comprising a second plurality of light-sensing regions located on a reverse side of the view-through sensor, wherein the obverse and reverse sides are opposite one another.

13. The apparatus according to claim 12, wherein the second plurality of light-sensing regions are in registration with corresponding respective ones of the first plurality of light sensing regions.

14. The apparatus according to claim 13, wherein the machine-executable instructions further comprise machine-executable instructions that, when executed by the processor, perform a calibration process that includes correlating corresponding respective ones of the first and second pluralities of light-sensing regions with one another for a particular user.

15. The apparatus according to claim 14, wherein the calibration process is performed when the pupil of the subject eye of the user is located in a center-pupil position.

16. The apparatus according to claim 13, wherein the machine-executable instructions further comprise machine-executable instructions further comprising a processor and comprise machine-executable instructions that, when executed by the processor, perform an eye-tracking process that includes using: pairs of light-intensity readings from the corresponding respective ones of the first and second pluralities of light-sensing regions; correlations between corresponding respective ones of the first and second pluralities of light sensing regions when the pupil of the subject eye is located in a center pupil position; and supervised learning to infer gaze of the eye.

17. The apparatus according to claim 11, wherein the machine-executable instructions further comprise machine-executable instructions that, when executed by the processor, perform a process that includes: prior to tracking, estimating, for each of the first plurality of light-sensing regions, light reflected from the exterior of the subject eye when the pupil is in a center-pupil position; during tracking, extracting features of changes in reflected light reflected from the subject eye associated with pupil position; and estimating a gaze vector using the features of changes in the reflected light.

18. The apparatus according to claim 17, wherein the machine-executable instructions further include machine-executable instructions that, when executed by the processor, perform blink detection simultaneously with the extracting of features of changes in the reflected light.

19. The apparatus according to claim 17, wherein the machine-executable instructions further include machine-executable instructions that, when executed by the processor, perform a process that includes: continually determining the intensity of the environmental light; and when the intensity of the environmental light is sufficient: extracting the features of the changes in the reflected light reflected from the subject eye associated with pupil position; and estimating the gaze vector using the features of changes in the reflected light.

20. The apparatus according to claim 11, wherein the machine-executable instructions further comprise machine-executable instructions further comprising a processor and comprise machine-executable instructions that, when executed by the processor, perform a method that includes: receiving, from offboard the apparatus, intensity information for the environmental light; and correlating the intensity information with the first plurality of light-sensing regions.

21. The apparatus according to claim 20, wherein the environmental light is from a device having video display that emits the environmental light, and receiving the intensity information includes receiving the intensity information from the device.

22. The apparatus according to claim 1, wherein the machine-executable instructions further comprise machine-executable instructions further comprise machine-executable instructions that, when executed by the processor, perform a process that includes: performing light sensing of light reflected from the subject eye; making an inference of a location of the pupil based on performing the light sensing; detecting whether or not the pupil is a state of fixation; and when the fixation has been detected, performing a predictive-inference algorithm to predict a location of the pupil.

23. The apparatus according to claim 22, wherein the machine-executable instructions further include machine-executable instructions that, when executed by the processor, perform a process that includes: when fixation has not been detected, detecting whether or not the pupil is in a saccade; when the saccade has been detected, performing light sensing and determining a location of the pupil based on the light sensing; and when a saccade has not been detected, performing the predictive-inference algorithm to predict a future location of the pupil.

24. The apparatus according to claim 22, wherein the machine-executable instructions further include machine-executable instructions that, when executed by the processor, perform a process that includes: detecting, based on the light sensing, whether or not the subject eye has been subjected to a blink; and when a blink has not been detected, determining a location of the pupil based on the light sensing.

25. The apparatus according to claim 1, further comprising a plurality of light-emitting regions located within the peripheral active device region and interposed with ones of the first plurality of light-sensing regions, each of the plurality of light emitting regions configured to emit at a frequency that reflects off of the exterior of the subject eye.

26. The apparatus according to claim 25, wherein the plurality of light-emitting regions comprise a plurality of corresponding respective light-emitting diodes.

27. The apparatus according to claim 25, wherein the frequency is a near-infrared frequency.

28. The apparatus according to claim 25, wherein the machine-executable instructions further comprise machine-executable instructions further comprising a processor and comprise machine-executable instructions that, when executed by the processor, perform a process of: activating the light-emitting regions sequentially; and for activation of each of the light-emitting regions sequentially, acquiring light-intensity readings from each of the first plurality of light-sensing regions.

* * * * *

UNITED STATES PATENT AND TRADEMARK OFFICE
CERTIFICATE OF CORRECTION

PATENT NO. : 11,307,656 B2  
APPLICATION NO. : 16/645363  
DATED : April 19, 2022  
INVENTOR(S) : Tianxing Li et al.

Page 1 of 1

It is certified that error appears in the above-identified patent and that said Letters Patent is hereby corrected as shown below:

In the Claims

In Column 44, Line 10, Claim 22, the words "further comprise machine-executable instructions" should be removed.

Signed and Sealed this
Twenty-first Day of June, 2022

Katherine Kelly Vidal
*Director of the United States Patent and Trademark Office*